US007570797B1

(12) United States Patent
Wang et al.

(10) Patent No.: US 7,570,797 B1
(45) Date of Patent: Aug. 4, 2009

(54) METHODS AND SYSTEMS FOR GENERATING AN INSPECTION PROCESS FOR AN INSPECTION SYSTEM

(75) Inventors: David Wang, Sunnyvale, CA (US); Patrick Huet, San Jose, CA (US); Tong Huang, Sunnyvale, CA (US); Martin Plihal, Pleasanton, CA (US); Adam Chien-Huei Chen, San Jose, CA (US); Mike Van Riet, Morgan Hill, CA (US); Stewart Hill, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 668 days.

(21) Appl. No.: 11/125,429

(22) Filed: May 10, 2005

(51) Int. Cl.
*G06K 9/00* (2006.01)

(52) U.S. Cl. ............... 382/145; 250/559.45; 356/237.4; 356/237.5; 382/143; 382/144; 702/83

(58) Field of Classification Search ................ 250/250, 250/306, 307, 310, 559.45; 356/237.4, 237.5, 356/394; 382/141, 144, 145, 149; 702/40, 702/81, 82, 83, 84
See application file for complete search history.

(56) References Cited

U.S. PATENT DOCUMENTS

| | | | |
|---|---|---|---|
| 6,611,728 B1 * | 8/2003 | Morioka et al. ............. 700/109 |
| 6,744,266 B2 * | 6/2004 | Dor et al. .................... 324/751 |
| 6,779,583 B1 * | 8/2004 | Fulton et al. ................. 164/4.1 |
| 6,792,366 B2 * | 9/2004 | Hosoya et al. ................ 702/83 |
| 6,792,367 B2 * | 9/2004 | Hosoya et al. ................ 702/83 |
| 6,799,130 B2 * | 9/2004 | Okabe et al. .................. 702/82 |
| 6,879,392 B2 * | 4/2005 | Sakai et al. .............. 356/237.4 |
| 6,919,564 B2 * | 7/2005 | Nara et al. ..................... 850/10 |
| 6,928,375 B2 * | 8/2005 | Ono et al. ...................... 702/81 |
| 6,959,251 B2 * | 10/2005 | Coldren et al. ................ 702/83 |
| 7,112,791 B2 * | 9/2006 | Nozoe et al. .................. 250/310 |
| 7,330,248 B2 * | 2/2008 | Sakai et al. .............. 356/237.4 |
| 2001/0017878 A1 * | 8/2001 | Nozoe et al. .................... 374/5 |
| 2003/0050761 A1 * | 3/2003 | Okabe et al. .................. 702/82 |
| 2003/0058444 A1 * | 3/2003 | Nara et al. ................... 356/394 |
| 2003/0195712 A1 * | 10/2003 | Ono et al. ...................... 702/81 |
| 2003/0213909 A1 * | 11/2003 | Nozoe et al. ................. 250/310 |
| 2005/0033538 A1 * | 2/2005 | Okabe et al. .................. 702/82 |
| 2005/0168730 A1 * | 8/2005 | Sakai et al. .............. 356/237.4 |
| 2005/0195396 A1 * | 9/2005 | Ono et al. .................... 356/394 |
| 2006/0082763 A1 | 4/2006 | Teh et al. |
| 2007/0288219 A1 * | 12/2007 | Zafar et al. .................... 703/14 |

OTHER PUBLICATIONS

U.S. Appl. No. 60/618,475 (Teh et al.) entitled Computer-Implemented Methods and Systems for Classifying Defects on a Specimen filed Oct. 12, 2004.

* cited by examiner

*Primary Examiner*—Gregory M Desire
(74) *Attorney, Agent, or Firm*—Ann Marie Mewherter

(57) ABSTRACT

Methods and systems for generating an inspection process for an inspection system are provided. One computer implemented method includes generating inspection data for a selected defect on a specimen at different values of one or more image acquisition parameters of the inspection system. The method also includes determining which of the different values produces the best inspection data for the selected defect. In addition, the method includes selecting the different values determined to produce the best inspection data as values of the one or more image acquisition parameters to be used for the inspection process.

20 Claims, 13 Drawing Sheets

| Spectrum | Visible | | | UV | | | NB |
|---|---|---|---|---|---|---|---|
| Imaging Mode | BF | EC | FS | BF | EC | FS | BF |
| 0.16 | ■ | ■ | ■ | ☑ | | ■ | ☑ |
| 0.20 | ■ | ■ | ■ | ☑ | | | |
| 0.25 | ☑ | ☑ | | ☑ | ☑ | | ■ |
| 0.39 | | | ■ | | | ■ | ■ |
| 0.62 | | | ■ | | | ■ | ■ |

Image Grab
Choose Optics for Image Grab:

Light Training: Recipe Care Area
Number of Locations: 4
Number of Images: 14

OK    Cancel

Fig. 4

Selected Optics Modes:
0.200 G-Line BrightField
0.200 I-Line BrightField
0.200 UltraViolet BrightField
0.200 UltraViolet EdgeContrast
0.200 UltraViolet EdgeContrast+
0.200 UltraViolet FullSky Remove Remove All

Fig. 5

New Images:    18 (6 modes * 3 sites - 0 already available)
Light Trainings:  6
Estimated Time:  2 minutes

Fig. 6

METHODS AND SYSTEMS FOR GENERATING AN INSPECTION PROCESS FOR AN INSPECTION SYSTEM

BACKGROUND OF THE INVENTION

1. Field of the Invention

The present invention generally relates to methods and systems for generating an inspection process for a semiconductor wafer or reticle inspection system. Certain embodiments relate to a computer-implemented method that includes selecting values of one or more image acquisition, sensitivity and nuisance removal parameters, which are determined to produce the best and most complete inspection data, to be used in the inspection process.

2. Description of the Related Art

The following description and examples are not admitted to be prior art by virtue of their inclusion in this section.

Inspection processes are used at various times during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Inspection for many different types of defects has also become more important recently. For instance, in order to use the inspection results to monitor and correct semiconductor fabrication processes, it is often necessary to know what types of defects are present on a specimen. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

Many different types of inspection systems have been developed to detect the different types of defects described above. In addition, most inspection systems are configured to detect multiple different types of defects. In some instances, a system that is configured to detect different types of defects may have adjustable image acquisition and sensitivity parameters such that different parameters can be used to detect different defects or avoid sources of unwanted (nuisance) events. For instance, the spot or pixel size, polarization or the algorithm settings for the angles of collection may be different for an inspection process used to detect particulate defects than for an inspection process used to detect scratches.

Although an inspection system that has adjustable image acquisition and sensitivity parameters presents significant advantages to a semiconductor device manufacturer, these inspection systems are useless if the incorrect image acquisition and sensitivity parameters are used for an inspection process. For example, incorrect or non-optimized image acquisition and sensitivity parameters may produce such high levels of noise that no defects can be detected in the generated inspection data. In addition, since the defects, process conditions and noise on a specimen such as a reticle and a wafer may vary dramatically (and since the characteristics of the specimen itself may vary dramatically), the best image acquisition and sensitivity parameters for detecting the defects on a particular specimen may be difficult, if not impossible, to predict. Therefore, although using the correct image acquisition and sensitivity parameters will have a dramatic effect on the results of inspection, it is conceivable that many inspection processes are currently being performed with incorrect or non-optimized image acquisition and sensitivity parameters.

The task of setting up an inspection process for a particular specimen and a particular defect of interest may be extremely difficult for a user particularly when an inspection system has a relatively large number of adjustable image acquisition settings and sensitivity parameters. In addition, it may be impossible to know whether the best inspection process has been found unless all possible combinations of the image acquisition parameters have been tested. However, most inspection processes are currently set up using a large number of manual processes (e.g., manually setting the image acquisition parameters, manually analyzing the resulting inspection data, etc.). As such, setting up the inspection process may take a relatively long time. Furthermore, depending on the types of specimens that will be inspected with the inspection system, a different inspection process may need to be set up for each different type of specimen. Obviously, therefore, setting up the inspection processes for all of the different specimens that are to be inspected may take a prohibitively long time.

Even with the correct image acquisition settings, algorithms for separating the defects from the noise and nuisance events need to be tuned for optimal inspection performance.

In some cases, the user may not know the operating range of a sensitivity parameter, which can lead to beginning the setup process with one or more sensitivity parameter settings in a state which will lead to excessive numbers of defects, or one that will not be sufficiently sensitive.

Accordingly, it may be advantageous to develop methods and systems for generating an inspection process for an inspection system that reduce the burden of setting up the inspection process on the user while increasing the optimization of the parameters of the inspection process and decreasing the time involved in generating the inspection process.

SUMMARY OF THE INVENTION

The following description of various embodiments of methods and systems for generating an inspection process for an inspection system is not to be construed in any way as limiting the subject matter of the appended claims.

One embodiment relates to a computer-implemented method for generating an inspection process for an inspection system. The method includes generating inspection data for a selected defect on a specimen at different values of one or more image acquisition parameters of the inspection system. The method also includes determining which of the different values produces the best inspection data for the selected defect. In addition, the method includes selecting the different values determined to produce the best inspection data as values of the one or more image acquisition parameters to be used for the inspection process.

In one embodiment, the method may include generating initial inspection data for the specimen with the inspection system. In one such embodiment, the method also includes identifying the selected defect in the initial inspection data, which includes detecting multiple defects on the specimen having the greatest diversity of one or more characteristics of the multiple defects. In a different such embodiment, the method includes identifying a plurality of the selected defects in the initial inspection data, which includes locating a first of the selected defects and searching for a second of the selected defects based on the initial inspection data associated with the first of the selected defects.

In another embodiment, the best inspection data includes the inspection data having the highest signal-to-noise ratio for the selected defect or the best separation between the selected defect and noise in the inspection data. However, the best inspection data may include inspection data having any other maximum or minimum characteristic.

In an additional embodiment, the different values correspond to one or more tests that can be performed on the specimen by the inspection system. In one such embodiment, the inspection process includes the one or more tests. In a further embodiment, the values of the one or more image acquisition parameters to be used in the inspection process include values for two or more tests to be performed with different image acquisition modes in the inspection process.

In another embodiment, the method includes identifying available options for the different values of the one or more image acquisition parameters and displaying the available options to a user for selection. In some embodiments, the different values and the one or more image acquisition parameters are selected by a user for use in the inspection process. In other embodiments, the different values and the one or more image acquisition parameters are selected without input from a user. Each of the embodiments of the method described above may include any other step(s) described herein.

Another embodiment relates to a different computer-implemented method for generating an inspection process for an inspection system. This method includes generating data for a specimen at different values of one or more sensitivity parameters of the inspection process. The method also includes displaying the data such that a user can select a value of the data. In addition, the method includes selecting values of the one or more sensitivity parameters to be used for the inspection process based on the value of the data selected by the user.

In one embodiment, the selecting step is performed by the user with assistance from the computer-implemented method. In another embodiment, the method includes collecting statistics on performance of the one or more sensitivity parameters across multiple subdivisions of an inspected area on the specimen without any prior knowledge or assumption of initial values of the one or more sensitivity parameters. In one such embodiment, the method includes automatically determining the initial values for the one or more sensitivity parameters based on the statistics. The initial values may be used to determine the different values of the one or more sensitivity parameters, and the generating step may include detecting events in each of the multiple subdivisions. In a different such embodiment, the method may include displaying a summary of the statistics such that the user can select the initial values for the one or more sensitivity parameters. In another such embodiment, the method includes automatically selecting the initial values for the one or more sensitivity parameters based on the statistics.

In another embodiment, the method includes performing the inspection process on the specimen to generate additional inspection data, applying a sequence of rules for defects to the additional inspection data, classifying the defects based on results of the applying step, and tuning a threshold value of the inspection process based on results of the classifying step. In a different embodiment, the method includes performing the inspection process on the specimen to generate additional inspection data, applying a sequence of rules for defects to the additional inspection data with different values for one or more parameters of at least one of the sequence of rules, classifying the defects based on results of the applying step, and displaying results of the classifying step such that a user can select values for the one or more parameters to be used with the inspection process.

In an additional embodiment, the method includes selecting values for one or more parameters of a filter for the inspection process. The filter is configured to remove nuisance defects from the inspection data. In a further embodiment, the method includes performing the inspection process two or more times on at least a portion of the specimen to produce two or more sets of additional inspection data and identifying defects that appear in a number of the two or more sets that is less than a predetermined number as nuisance defects. In one such embodiment, the method includes tuning a threshold for the inspection process based on results of the identifying step. Each of the embodiments of the method described above may include any other step(s) described herein.

Another embodiment relates to a carrier medium that includes program instructions that are executable on a computer system for performing a method for generating an inspection process for an inspection system. The method includes generating data for a specimen at different values of one or more parameters of the inspection system. The one or more parameters include one or more image acquisition parameters, one or more sensitivity parameters, or some combination thereof. The method also includes determining which of the different values produces the best data for the specimen. In addition, the method includes selecting the different values determined to produce the best data as values of the one or more parameters to be used for the inspection process. The method may include any other step(s) described herein. The carrier medium and the program instructions may be further configured as described herein.

An additional embodiment relates to a system configured to generate an inspection process. The system includes an inspection system that is configured to generate data for a specimen at different values of one or more parameters. The one or more parameters include one or more image acquisition parameters, one or more sensitivity parameters, or some combination thereof. The system also includes a computer system configured to determine which of the different values produces the best data for the specimen. The computer system is also configured to select the different values determined to produce the best data as values of the one or more parameters to be used for the inspection process. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIGS. 2-9 are screenshots illustrating examples of different user interfaces that can be used to select values of one or more image acquisition parameters to be used for an inspection process;

Figure 1:
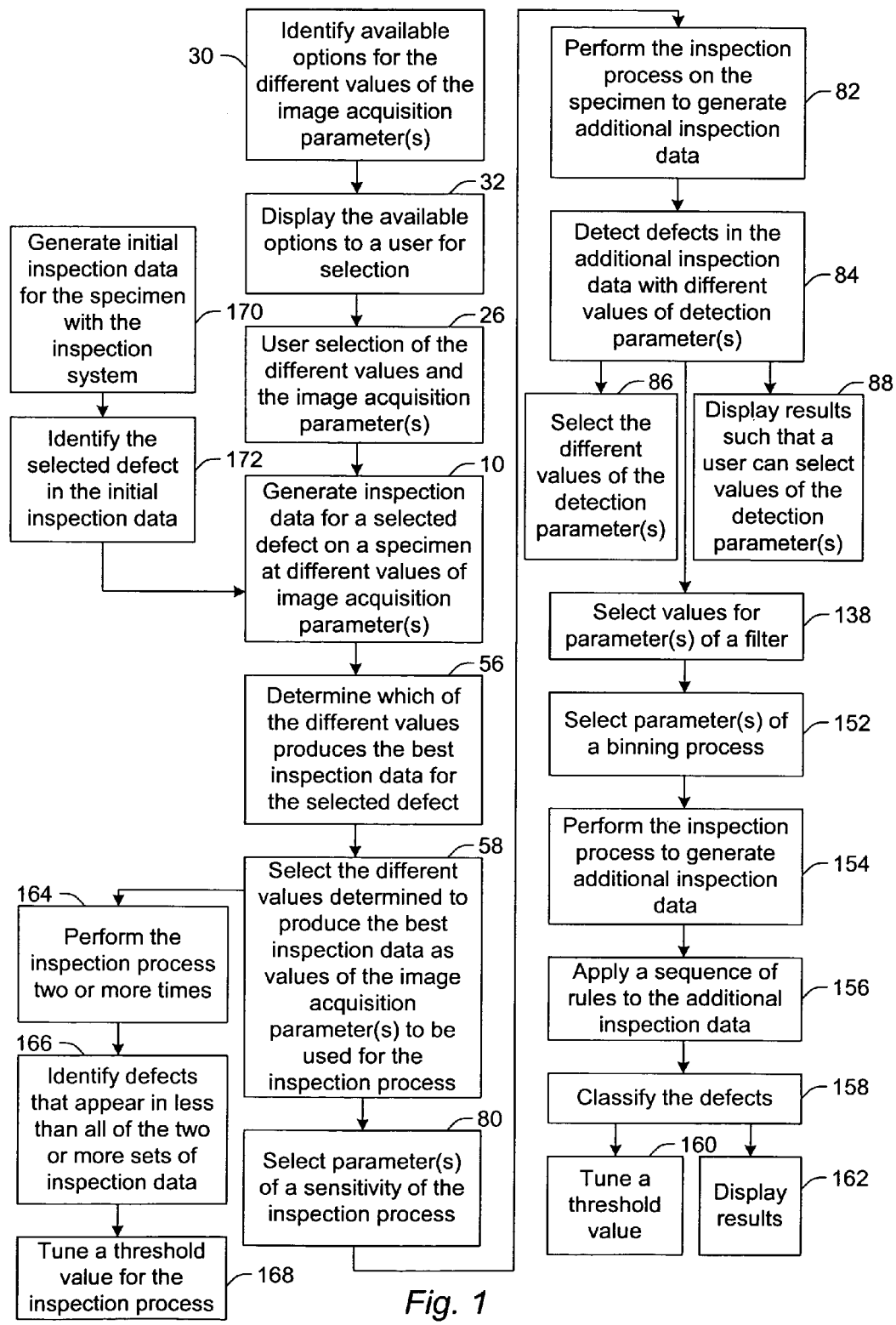
FIG. 1 is a flow chart illustrating one embodiment of a computer-implemented method for generating an inspection process for an inspection system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having a layer of opaque material formed thereon. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used herein to generally refer to semiconductor devices such as integrated circuits and other devices such as microelectromechanical (MEMS) devices and the like, which may be formed on a wafer.

The creation of wafer inspection recipes can take many hours. Setting up the inspection test (or tests) dominates the recipe creation process time. There are four points in the test creation process that consume most of the time. The first is finding the defects of interest (DOI). In some cases, the locations of the DOI will be known, perhaps from inspection results from another tool. If so, these locations can be used to move to the next step. However, this prior knowledge does not always exist, particularly for highly sensitive tools. The second point that consumes much of the recipe creation process time is selecting the image acquisition conditions that will maximize the overall signal-to-noise ratio (S/N). The third point is tuning the algorithms that control sensitivity and reduce the occurrence of nuisance events and defects that are not of interest. The fourth point is setting up the recipe that will be used to bin the defects that are found into useful groups for the purpose of sampling at high resolution image acquisition or scanning electron microscopy (SEM), or of trending the results to identify excursions from normal operations.

There are additional disadvantages of the currently used methods for setting up an inspection recipe. For instance, it is difficult to find the DOI if the locations are not known a priori, and finding the DOI is central to setting up an effective inspection process. In addition, once the DOI is found, the task of finding the second and third instances of the same DOI is just as difficult as finding the first. In addition, the results of the DOI finding do not easily persist through the other steps of setting up a recipe.

Other disadvantages of the methods are due to the currently used methods for setting up the sensitivity of the inspection process. For example, current methods for determining the real and noise/nuisance events for sensitivity tuning rely solely on aspects of the defect appearance, and other attributes are not used. This sole reliance on the defect appearance has two negative effects. First, on many occasions, only a subset of the appearance based features are relevant in determining which defects are relevant. The other features are "noise" and result in a poor separation of defects for tuning the threshold. Second, on many occasions, a combination of attributes and appearance are more effective in binning defects than appearance alone as described in co-pending, commonly assigned U.S. Patent Application Ser. No. 60/618,475 to Teh et al. filed on Oct. 12, 2004, which is incorporated by reference as if fully set forth herein. In addition, current methods for performing sensitivity tuning require user confirmation of the nuisance and real defects, which takes more time than is needed for the foundry use case.

Further disadvantages of the methods are due to the currently used methods for setting up the binning method for the inspection process. For example, in current methods, the user does not get full feedback on the value settings for the rule-based nodes used in the binning process.

The methods and systems described herein are intended to reduce the time involved in performing the steps for setting up an inspection process while improving the effectiveness of those steps for various conditions. The components of the methods may include a sequence of steps to find instances of DOI efficiently, which may be configured for finding sufficient examples of DOI through sampling and analysis. DOI finding may include a step such as "Diverse Sampling," "Defects Like Me," "Defects Like Us," "Regions Like Us," etc., and Zap (remove) Defects, which are described further herein. The components of the method may also include user assisted selection of the image acquisition parameters for the inspection process. In addition, the components may include binning results from a preliminary inspection to improve the effectiveness and speed of sensitivity tuning. The components may further include noise identification using non-repeatability of noise for sensitivity tuning and/or a sensitivity training approach for tuning binning recipes.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates an embodiment of a computer-implemented method for generating an inspection process for an inspection system. It is noted that many of the steps shown in FIG. 1 are not essential to practice of the method. In particular, one or more steps may be omitted or added to the method illustrated in FIG. 1, and the method can still be practiced within the scope of this embodiment. In addition, many of the steps shown in FIG. 1 do not have to be performed in the order shown in FIG. 1. In particular, the steps may be performed in any order unless otherwise noted herein. Furthermore, although the embodiments of the method are described herein with respect to images, it is to be understood that the methods may be performed for any type of inspection data.

As shown in step 10 of FIG. 1, the method includes generating inspection data for a selected defect on a specimen at different values of one or more image acquisition parameters of an inspection system. The inspection system may be configured as described herein. In addition, the inspection system may have any configuration known in the art. Preferably, the inspection system has one or more adjustable image acquisition parameters. In addition, the inspection system may be configured for inspection of a wafer or another specimen such as a reticle. Furthermore, the methods described herein may be performed to generate a recipe for a system other than an inspection tool. For example, the methods described herein may be performed to generate a recipe for a review tool. Moreover, although the methods are described herein with respect to optical systems, it is to be understood that the methods may also be used to generate a process for a non-optical system having one or more adjustable data acquisition parameters such as, but not limited to, a scanning electron microscope (SEM).

Figure 2:
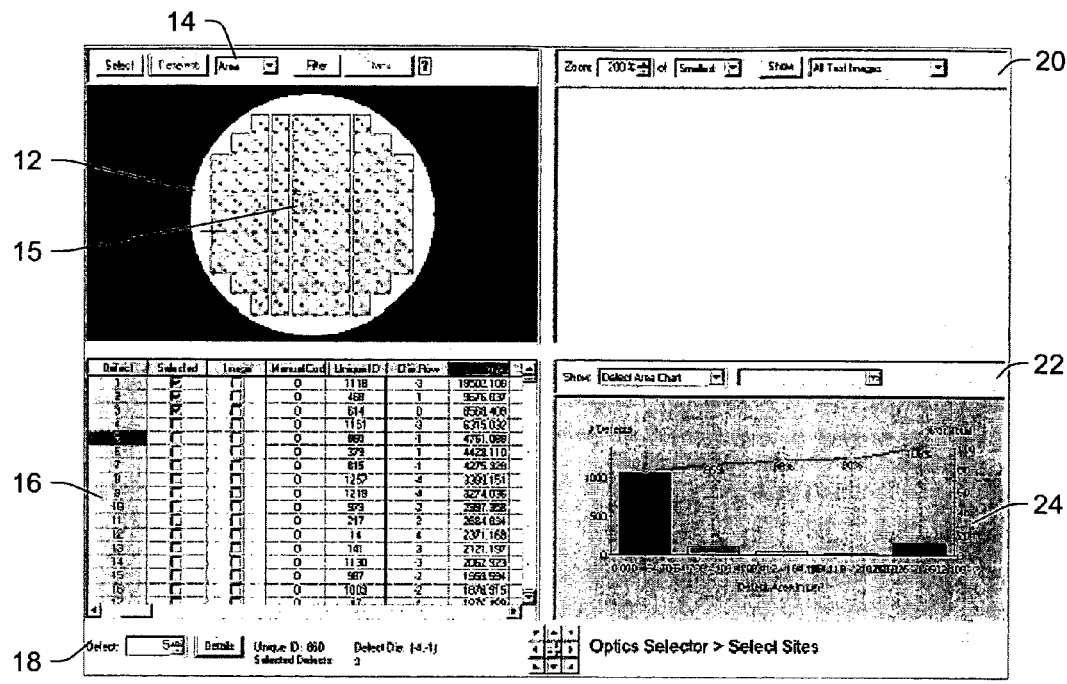

FIG. 2 is a screenshot that illustrates one example of a user interface that can be used to select the defects on a specimen for which inspection data will be generated at different values of image acquisition parameter(s) of the inspection system. It is noted that all of the screenshots that are illustrated and described herein are merely presented as examples of user interfaces that can be used to implement the methods described herein to further understanding of the methods. Obviously, many different configurations for the user interfaces are possible, and all such configurations are within the scope of the present disclosure.

As shown in FIG. 2, the user interface displays defect map 12, which indicates the locations of potential defects on a specimen. The specimen in this example is a wafer. The defect map that is shown in FIG. 2 may include a lot result, which may be selected by the user in any manner. The user interface also allows a user to select the defects in different manners. For instance, as shown in FIG. 2, the user may choose to select defects within area 14. Upon selection of area 14, the user will be able to select a particular area (e.g., area 15) on the specimen such that inspection data will be generated at different values of image acquisition parameter(s) of an inspection system for the defects located in the particular area. Although only one area is selected in FIG. 2, it is to be understood that the user interface may be configured such that the user can select more than one area on the specimen.

As further shown in FIG. 2, the user interface presents above the defect map a number of other options for the user that can be used to perform one or more functions. For example, after the user has selected one or more defects, the Deselect option may be available, which the user can select to revise his/her defect selections. In addition, the Filter option may be available, which can be selected to filter the defects in the defect map. Filtering can be performed as described further herein. The user interface may also display Stack option to the user, which may be available for selection depending on the type of inspection that was performed on the specimen. The Stack option can be used to overlay different portions of the defect map such that the different portions may be compared (e.g., for repeating defects).

As further shown in FIG. 2, this user interface includes table 16 listing information about the defects that were found on the specimen. Table 16 may include a variety of information in columns such as, from left to right in the table, defect number, an indication of whether or not the defects were selected by the user, an indication of whether or not an image of the defect is selected, a manual classification code, a unique identifier for the defects, the die row in which the defects are located, and the greatest area of the defects. Obviously, the table may include less than this information, some of this information with other possible information about the defects, or other information. The user may use the table to select individually those defects for which inspection data will be generated at different values of the image acquisition parameter(s) of the inspection system. Therefore, the user can select defects collectively in the defect map as described above or individually using the table. As further shown in FIG. 2, information 18 about a defect may be illustrated when a defect is selected, for example, by clicking on one of the defect numbers shown in the table.

The user interface of FIG. 2 may include additional information and options for the user. For instance, the user can choose to view one or more of the detected defects using the options in tool bar 20, which may include, from left to right, zoom, defect type or sorting method (e.g., smallest), and the type of information to be shown (e.g., all test images, etc.). In addition, the user interface may be used to display other information about the defects using options in tool bar 22, which in one example includes a defect area chart. Defect area chart 24 includes, in the illustrated example, a bar chart showing the number of defects as a function of a defect area range.

After the user has selected sites or defects, the computer-implemented method includes selecting the different values and the one or more image acquisition parameters to be evaluated as described further herein. As shown in step 26 of FIG. 1, the different values and the image acquisition parameter(s) may be selected by a user. In addition, the different values and the image acquisition parameter(s) may be selected by a user with assistance from the computer-implemented method as described further herein. Alternatively, the different values and the image acquisition parameter(s) may be selected without input from a user (e.g., automatically) by the computer-implemented method.

The computer-implemented methods described herein, therefore, provide a number of advantages over previously used methods for generating an inspection process for an inspection system. For example, most modern wafer inspection and review systems offer a variety of choices in the image acquisition system such as illumination conditions (e.g., intensity, wavelength(s), and polarization for image acquisition tools), focus, detector polarization for image acquisition tools, pixel size including setting lens combinations, filtering modes (such as Fourier, Neutral Density, Edge Contrast, or Full Sky), and digitization settings such as gain and offset. Without guidance, it is extremely difficult for the user to know which combination of the many possible settings will provide an optimal S/N or other optimal inspection data characteristic at an acceptable throughput.

On some commercially available inspection systems such as the AIT tools that are commercially available from KLA-Tencor Corporation, San Jose, Calif., an off-line image acquisition optimization tool was developed to assist in the selection of image acquisition parameters for an inspection process. In this tool, a user manually acquires small scans of data (which have been called "mini-strips") at different polarization combinations for illumination and detection and different illumination intensities. The tool then helps select the optimal settings for these variables. Alternatively, the data gathering can be performed automatically, but the analysis is off-line and does not cover all of the possible image acquisition settings automatically.

The methods described herein, however, are adaptable to cover all applicable image acquisition parameters for a given inspection or review system, and the entire sequence of choosing settings, gathering data, and evaluating the results can be automated. The methods described herein may be implemented on existing inspection and/or review systems such as the 23xx tool, which is commercially available from KLA-Tencor. However, the methods described herein can be implemented on any inspection and/or review system with considerations for the unique capabilities and constraints of different systems.

Figure 3:
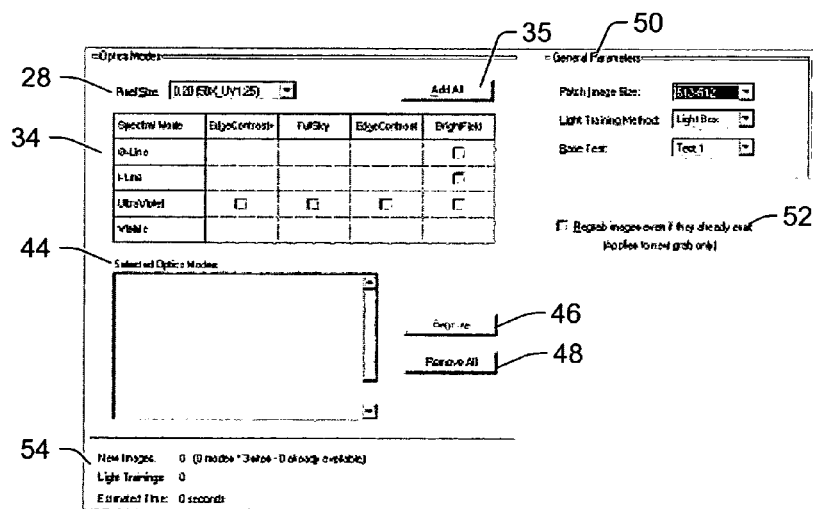

FIG. 3 illustrates one example of a user interface that is configured to allow a user to select the different values and the image acquisition parameter(s). As shown in FIG. 3, the user interface includes Pixel Size option 28. The user can select a pixel size from a pixel size drop down list. The pixel size drop down list may be populated automatically by the computer-implemented method based on the characteristics of the inspection system.

In this manner, the method may include identifying available options for the different values of the image acquisition parameter(s) (e.g., pixel size), as shown in step 30 of FIG. 1. In addition, the method may include displaying the available options to a user for selection, as shown in step 32 of FIG. 1. In another example, as shown in FIG. 3, the user interface also includes spectral modes grid 34. The spectral modes grid is populated with the valid options that are available for the pixel size selected by the user. In the example of FIG. 3, the spectral modes grid includes different values for illumination wavelengths of the inspection system in the rows (e.g., from top to bottom, G-line, I-line, UltraViolet, and Visible) and different values for the type of illumination in the columns (e.g., from left to right, Edge Contrast +, Full Sky, Edge Contrast, and Bright Field).

Obviously, the spectral modes grid may be populated for other parameters of interest for the inspection process. In addition, the values of the parameters that are shown in the spectral modes grid will vary depending on the configuration of the inspection system. The available spectral modes are indicated in FIG. 3 by a box, which can be selected by the user to indicate which spectral modes are to be evaluated in the method. Alternatively, the user may select all of the available options shown in spectral modes grid 34 by selecting Add All button 35 illustrated above the spectral modes grid. In any case, the different values of the image acquisition parameter(s) evaluated by the method may correspond to one or more tests that can be performed on the specimen by the inspection system.

FIG. 4 illustrates another example of a spectral modes grid that may be populated as described above. As shown in FIG. 4, spectral modes grid 36 includes spectrum options 38, which include in this example Visible, ultraviolet (UV), and narrow band (NB). In addition, the spectral modes grid illustrates available imaging modes 40 that can be used with each spectrum option, which include in this example bright field (BF), edge contrast (EC), and full sky (FS) for the visible and UV spectrums and BF for the NB spectrum. The rows in the spectral modes grid correspond to different pixel sizes available for the inspection system. The pixel sizes are shown in units of microns. The different values and the image acquisition parameters included in the spectral modes grid may vary depending on, for example, the configuration of the image acquisition system. For example, the spectral modes grid shown in FIG. 4 may be suitable for the 23xx system that is commercially available from KLA-Tencor, and other spectral modes grids may be populated differently for other inspection systems.

The computer-implemented method may determine the available options for the different values of the image acquisition parameters and display the available options to the user in the spectral modes grid. For example, as shown in FIG. 4, the cells in spectral modes grid 36 that are not darkened indicate available options identified by the method that can be selected by a user. The user may select one or more of the available options, for example, by selecting one or more of the cells as shown in FIG. 4. In addition, as shown in FIG. 4, the user can select a Light Training option to be used with the selected values of the optional parameter(s) from drop down menu 42. As further shown in FIG. 4, this user interface also displays the number of locations that have been selected for inspection data generation and the number of images to be generated at each location. If the user is satisfied with his/her selections in spectral modes grid 36 and drop down menu 42, the user may select OK. Otherwise, the user may select Cancel to close this user interface without saving the previously selected values of the image acquisition parameter(s).

Upon selection of one or more of the spectral modes in spectral modes grid 34 or 36, the selected spectral modes may be listed in Selected Optics Mode list 44, which is shown in FIG. 3. One example of a list of selected spectral modes in Selected Optics Mode list 44 is shown in FIG. 5. The user may edit the selected spectral modes, by selecting one of the spectral modes in the list and then selecting Remove option 46, as shown in FIGS. 3 and 5. In addition, the user may select Removal All option 48, which will delete from the Selected Optics Modes list all of the spectral modes that have been selected up to that point.

As shown in FIG. 3, the user interface may present additional options for the values of the image acquisition parameter(s) that will be evaluated. For example, the user may select one or more General Parameters 50 from a plurality of drop down menus. The General Parameters may include, for example, Patch Image Size, Light Training Method, and Base Test. Patch Image Size determines the size of the images that will be "grabbed." The Light Training Method determines the method that will be used to train light of the inspection system before the images are grabbed. The Base Test determines the test to be used for image grabbing. Like the values of the other image acquisition parameters that are presented to the user in the user interface, the available options that populate these drop down menus may be generated automatically based on, for example, characteristics of the selected defects and characteristics of the inspection system. In addition, the user interface shown in FIG. 3 includes option 52, which allows the user to select if images should be "re-grabbed" even if the images already exist, which applies to the next image grab only.

As further shown in FIG. 3, upon selection of the different values of the one or more image acquisition parameters of the inspection system that are to be evaluated, the user interface displays information 54. Information 54 can be modified as the different values of the one or more image acquisition parameters are selected. For instance, as shown in FIG. 3, this information may include only the number of sites selected for generation of the inspection data or image "grab" since no values of the image acquisition parameters have yet been selected. However, as shown in FIG. 6, after one or more different values of the image acquisition parameter(s) have been selected, the information may include the number of New Images that will be grabbed, which as shown in FIGS. 3 and 6 is the number of image acquisition modes selected times the number of sites to be inspected minus the number of images that are already available. In addition, information 54 illustrates the number of different Light Training methods that will be used to train light of the inspection system before generation of the inspection data. Information 54 also displays the Estimated Time for grabbing all of these images. In this case, the estimated time is only 2 minutes. Obviously, information 54 that is illustrated in FIG. 3 may vary and may include more information about the inspection data generation that will be performed based on the user selections.

Although the embodiments described above are configured for user-assisted selection of the different values of the one or more image acquisition parameters that are to be evaluated as described herein, the different values and the one or more image acquisition parameters may be selected without input from a user. For example, based on the selected defects, the computer-implemented method may be configured to determine which of the different values of the image acquisition parameter(s) may be suitable for generating inspection data for the selected defects. In one such particular example, the computer-implemented method may include using a set of rules to determine which of the different values of the image acquisition parameter(s) will be evaluated based on one or more characteristics of the selected defects and the configurations available on the inspection system.

After selection of the different values and the one or more image acquisition parameters, the method includes generating the inspection data for these different values and image acquisition parameter(s), as shown in step 10 of FIG. 1. Generating the inspection data shown in step 10 may include "grabbing" images of the selected defect(s) at the different values of the image acquisition parameter(s). Most likely, the image grab will be performed for each of the selected defects with a first set of values for the image acquisition parameters of the inspection system. The image acquisition parameters of the inspection system may then be altered to the next set of values for the image acquisition parameters, and the image grab may be repeated for each of the selected defects. These steps can be repeated for each of the different values of the image acquisition parameter(s) that are selected for evaluation.

Figure 7:

Referring back to FIG. 1, the method also includes determining which of the different values produces the best inspection data for the selected defect, as shown in step 56. In addition, the method includes selecting the different values determined to produce the best inspection data as values of the one or more image acquisition parameters to be used for the inspection process, as shown in step 58 of FIG. 1. In one such embodiment, the method may include displaying the generated inspection data in a user interface such as user interface 60 shown in FIG. 7. As shown in FIG. 7, each of the images for the selected defects that were generated in step 10 of FIG. 1 at different values of image acquisition parameter(s) of the inspection system may be displayed. In this manner, images of a selected defect grabbed for multiple image acquisition modes may be displayed. In the particular example of FIG. 7, images of selected defects 1 and 22 generated for image acquisition modes 1, 2, and 3 are displayed in the user interface in an arrangement that allows for relative ease of comparison of the images.

The user may view the displayed images and select the best image of a selected defect (i.e., the best inspection data for the selected defect). In addition, one or more characteristics of each of the images of the selected defects may be determined by the computer-implemented method and displayed in the user interface. In this example, the S/N for each of the defect images is illustrated under the corresponding image. In this manner, the user may select the best image based on the illustrated characteristic. It is to be understood that any meaningful characteristic of the inspection data (e.g., signal, noise, etc.) may be illustrated in user interface 60. In addition, more than one characteristic for the defect images may be illustrated in the user interface. These characteristics of the inspection data may be determined in any manner known in the art. Therefore, the method may be configured for user-assisted selection of the best inspection data.

As shown in FIG. 7, the best inspection data for different types of defects may not be produced by the same values of the image acquisition parameter(s) of the inspection system. In particular, as shown in FIG. 7, mode 2 produced the highest S/N for defect 1. In contrast, mode 3 produced the highest S/N for defect 22. In this manner, the user interface may be configured to allow the user to select independently the best inspection data for each selected defect. If the values that produced the best inspection data are different for the selected defects, the computer-implemented method may include generating a separate test for each of the selected defects that is to be performed with the values corresponding to the best inspection data selected by the user. In this manner, the inspection process may include one or more tests. In addition, the values of the one or more image acquisition parameters that are to be used in the inspection process may include values for two or more tests that are to be performed with different image acquisition modes in the inspection process.

Figure 8:
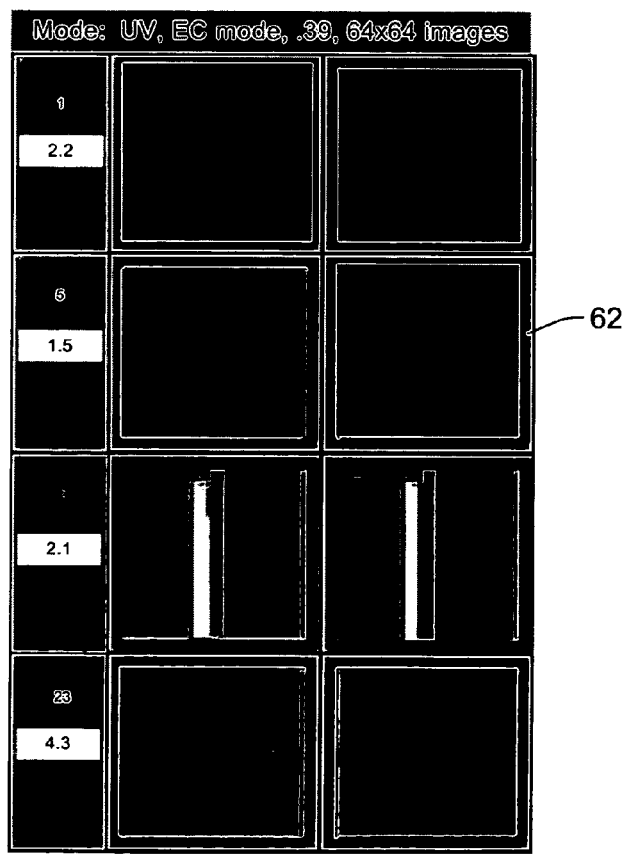

In another example, images grabbed for different defects in a single mode may be displayed in user interface 62 shown in FIG. 8. In this particular example, images for different types of selected defects are displayed, each of which was generated for the same values of the image acquisition parameters of the inspection system. Particularly, the images shown in the user interface of FIG. 8 were generated with UV light, EC image acquisition mode, a pixel size of 0.39 micron, and a patch size of 64 pixels×64 pixels as displayed above the images. In this manner, the inspection data for multiple types of selected defects may be compared at the same values of the image acquisition parameters.

Such a comparison may be particularly useful when multiple types of defects are to be detected on a single specimen. For example, it may be determined that the values of the image acquisition parameters shown in FIG. 8 are suitable for detection of one or more, but not all, of the different types of defects. In this manner, these values of the image acquisition parameters may be used for one test of the inspection process. Other values of the image acquisition parameters may be evaluated in a similar manner, and it may be determined that these other values of the image acquisition parameters may be suitable for detection of other types of the selected defects. In this manner, these other values of the image acquisition parameters may be selected for another test that is to be performed in the inspection process. As such, the method may include determining which of the different values produces the best inspection data for different types of selected defects, and the different values of the image acquisition parameter(s) may be selected for different tests such that all of the different types of defects can be detected in a single inspection process. Therefore, the values of the one or more image acquisition parameters that are selected for use in the inspection process may include values for two or more tests to be performed with different image acquisition parameter settings in the inspection process.

Figure 9:
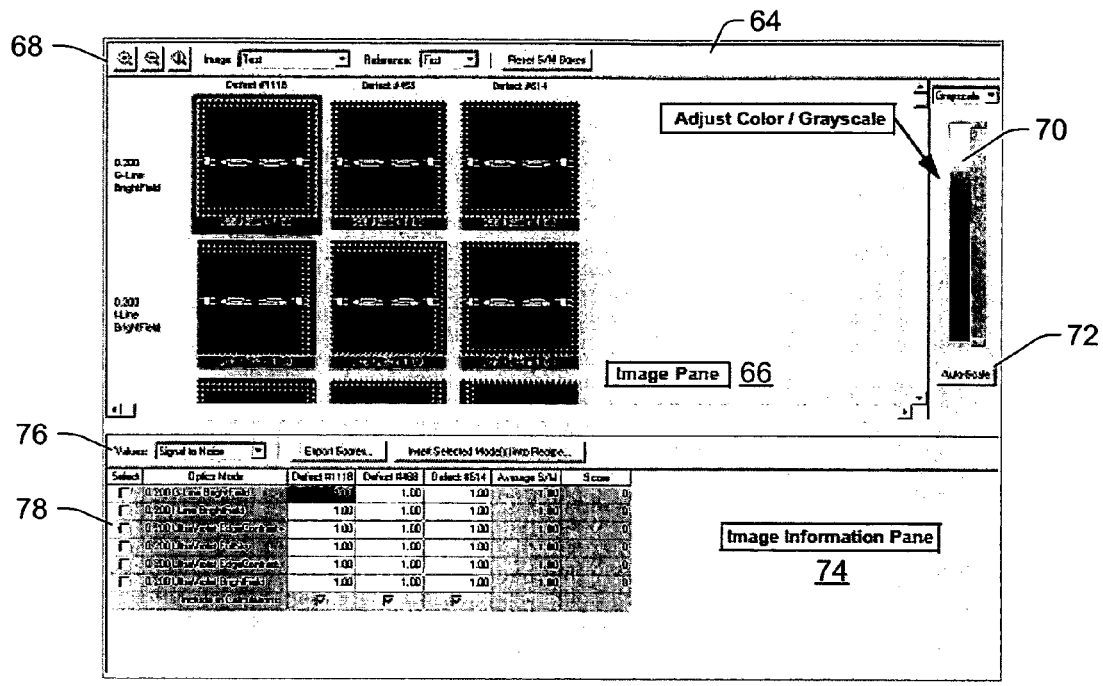

FIG. 9 illustrates another user interface that can be used to display the results of step 10 of the method. For example, user interface 64 includes Image Pane 66. Image Pane 66 displays all of the grabbed images. In this example, images grabbed for different selected defects (e.g., Defect #1118, Defect #468, and Defect #614) are shown in columns, and the rows of each of the columns correspond to the different values of the image acquisition parameter(s) (e.g., 0.200 G-Line Bright Field, 0.200 I-line Bright Field, etc.) that were used to grab the images.

Each of the displayed images also includes two boxes (indicated by the dotted lines shown in the images), one for selecting the signal area, and the other for selecting the noise. These boxes are re-sizable and can be individually set for each defect. Changing the Signal and/or Noise for a defect affects all of the images for the defect. The boxes may be illustrated in different colors to indicate which box is for the signal and which box is for the noise. In addition, an Analyze button (not shown) may be displayed in user interface 64, for example, in an Optics Setting sub menu (not shown), which when selected by the user will result in the image scores being recalculated. This analysis may be performed when the user changes the signal box and/or the noise box and wants to recalculate the scores for the new settings. It is noted that selecting the Analyze button will not re-grab the images. Selection of the Analyze button will only result in recalculation of the scores for the current images.

The user may right click on the Image Pane to display a context menu (not shown) from which the user can choose the type of image that is displayed. The types of images that are available for display may include, but are not limited to, test image, reference image, difference image, blink test/reference, and blink test/difference. Selecting either blink test/reference or blink test/difference menu items results in the respective images being changed in quick succession until a different menu item is selected. Image types can also be changed from tool bar 68 located in user interface 64 on top of image pane 66. The tool bar provides the user with buttons to zoom in, zoom out, zoom to 100%, and Reset S/N Boxes.

User interface 64 also includes Adjust Color/Grayscale pane 70. The Adjust Color/Grayscale pane provides a slider to adjust the color/grayscale values for one or more of the images. For example, the user can map the values in the images to color or grayscale values. The range of the color or grayscale values can be selected by moving the top and bottom slider controls. A choice between mapping of color or grayscale is provided in the drop down list located at the top of pane 70. In addition, the Adjust Color/Grayscale pane includes Auto Scale button 72, which the user can select to have the computer-implemented method automatically adjust the color/grayscale of the grabbed images. For example, selecting the Auto Scale button may result in automatic maximization of the dynamic range for mapping.

Image Information Pane 74 of user interface 64 displays information about the images. The Image Information Pane includes tool bar 76 that provides functionality and grid 78 that displays information such as scores for the images. In tool bar 76, a drop down menu may be used to select Values for which scores of the images are shown in the Image Information Pane. As shown in FIG. 9, one option for the image values is S/N. Other options include signal and noise. The scores calculated for S/N may be displayed by default. As shown at the bottom of grid 78, the Include in Calculation check box under the columns for each selected defect is provided to enable the user to select the defect information included in the calculation of the S/N value. When the check box for a defect is not selected, the information for that defect is not included in the calculation.

The information displayed in the Image Information Pane may be exported to a file such as a comma separated value (.csv) file for analysis. To export the scores, the user may select Export Scores button on tool bar 76, which may result in a Save As dialog box (not shown) being displayed. The exported information may be saved in any manner known in the art.

The Insert Selected Mode(s) into Recipe button shown in tool bar 76 is provided to allow the user to insert the selected optics mode(s) into a recipe. The selected mode(s) may include the mode(s) selected by the user as providing the best inspection data for the selected defects. The user may select the optics mode(s) to be inserted into the recipe by clicking the check box located in the Select column of the grid. Then, upon clicking the Insert Selected Mode(s) into Recipe button, a Save As dialog box (not shown) will be displayed, which allows the user to select the recipe into which the selected mode(s) will be inserted.

As described above, therefore, the user may select the best inspection data for a selected defect. In addition, the computer-implemented method may determine which of the different values correspond to the best inspection data as selected by the user and select these values for use in the inspection process. In an alternative embodiment, the computer-implemented method may select the best inspection data. For example, as described above, the method may include determining one or more characteristics of the inspection data such as S/N, signal, noise, etc., and these characteristics may be compared by the method to determine which inspection data has the best characteristic for a selected defect (e.g., the highest S/N, the highest signal, the lowest noise, etc.). In one particular embodiment, the best inspection data may include the inspection data having the highest S/N for the selected defect or the best separation between the selected defect and noise in the inspection data. The computer-implemented method may then determine which of the different values correspond to the best inspection data for the selected defect and select these values for use in the inspection process. In an alternative embodiment, the different values and the one or more image acquisition parameters are selected by a user for use in the inspection process.

Various investigations have shown that much of the time involved in setting up recipes with known best optics involves iterating over the parameter settings for sensitivity, and in particular finding the correct combinations of settings to detect defects near the "noise floor" and eliminate that noise from the defect population. Some of the following techniques are used on inspection systems commercially available from KLA-Tencor to handle noise, including segmented auto threshold (SAT) on bright field tools and XLAT and HLAT on dark field tools.

Referring back to FIG. 1, the method may include selecting one or more parameters of a sensitivity of the inspection process, as shown in step 80. In other words, the method may include tuning the sensitivity of the inspection process. Tuning the sensitivity of the inspection process as described herein will reduce the time and effort involved in configuring an inspection process in which the threshold is not fixed (e.g., in auto-threshold processes and SAT processes). Tuning the sensitivity of the inspection process preferably fine tunes the threshold or other algorithmic parameter values of the inspection process to improve the identification of real and/or killer defects while eliminating the detection of nuisance defects.

In one such embodiment, a computer-implemented method for generating an inspection process for an inspection system includes generating data for a specimen at different values of one or more sensitivity parameters of the inspection process. The method also includes displaying the data such that a user can select a value of the data. In addition, the method includes selecting values of the one or more sensitivity parameters to be used for the inspection process based on the value of the data selected by the user. Each of these steps of the method may be performed as further described herein. For instance, the selecting step may be performed by the user with assistance from the computer-implemented method as described further herein.

Figure 9A:
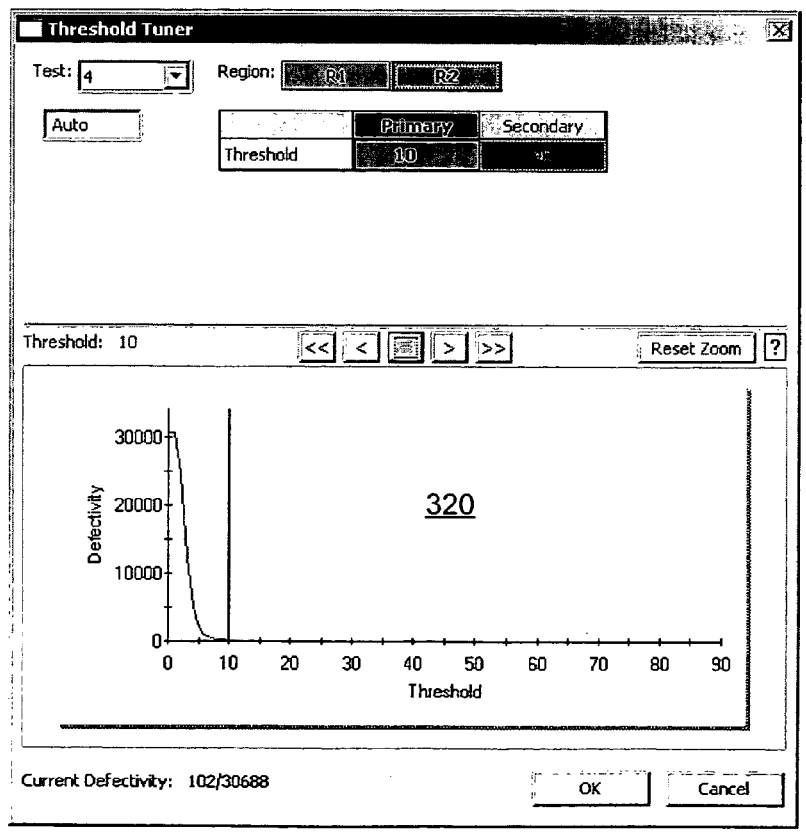
FIGS. 9a and 10-12 are screenshots illustrating examples of different user interfaces that can be used to select one or more sensitivity parameters of an inspection process.

In some cases, the user may be provided assistance in setting initial values for sensitivity parameters. As shown in the user interface of FIG. 9a, the method may include displaying the operating range of a sensitivity parameter over subdivisions of the inspected area to assist the user in determining the initial value for this parameter. In one embodiment, the method may include collecting statistics on performance of the one or more sensitivity parameters across multiple subdivisions of an inspected area on the specimen without any prior knowledge or assumption of initial values of the one or more sensitivity parameters. In one such embodiment, rather than showing defect count, this user interface displays graph 320 that shows the number of times one or more image differences are noted using this parameter over the subdivisions of the inspected area.

The method may also include automatically determining the initial values for the one or more sensitivity parameters based on the statistics. The initial values may be used to determine the different values of the one or more sensitivity parameters at which data is generated as described above. In some embodiments, generating the data for the specimen described above may include detecting events in each of the multiple subdivisions. In such embodiments, therefore, the method may include automatically selecting the initial values for the one or more sensitivity parameters based on the statistics. In an alternative embodiment, the method may include displaying a summary of the statistics such that the user can select the initial values for the one or more sensitivity parameters. For certain applications, the user may choose to use a setting where this parameter begins to provide some general sensitivity to defects. In other cases, the user may choose to use a more aggressive setting on this operating curve as a starting value for performing sensitivity tuning.

As further shown in step 82 of FIG. 1, the method may include performing the inspection process on the specimen to generate additional inspection data. The inspection process may be performed with the optimized values of the image acquisition parameter(s) for the inspection system, which are determined as described above. The method may also include detecting defects in the additional inspection data with different values of one or more detection parameters (e.g., one or more parameters of the sensitivity), as shown in step 84. In one such embodiment, the method may include selecting different values of the one or more detection parameters that result in detection of the greatest number of a selected type of defect to be used with the inspection process, as shown in step 86. Alternatively, selecting the different values of the detection parameter(s) for use in the inspection process may be based on any other characteristic of the detection results. In addition, selection of the different values of the detection parameter(s) may be based on more than one characteristic of the detection results. In this manner, the computer-implemented method may include automated selection of one or more parameters of the sensitivity of the inspection process.

Alternatively, the method may be configured for user-assisted selection of the parameter(s) of the sensitivity of the inspection process. For example, in a different embodiment, the method may include displaying results of the detecting step such that a user can select values of the detection parameter(s) to be used with the inspection process, as shown in step 88. In this manner, the computer-implemented method may configure the display of the detection results and assist the user in selection of one or more parameters of the sensitivity of the inspection process as described further herein.

Figure 10:
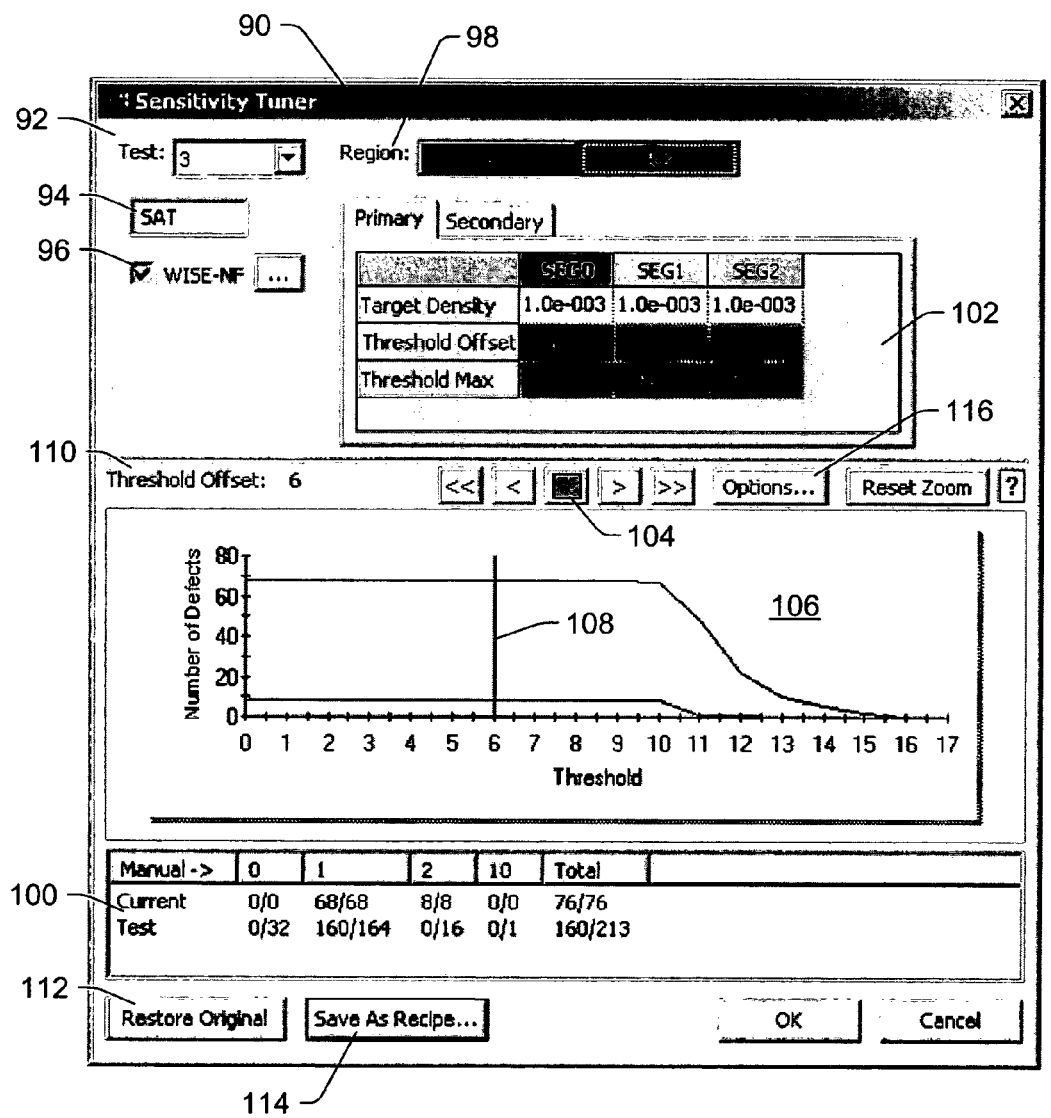

One example of a user interface that can be used to display and select parameter(s) of the sensitivity is illustrated in FIG. 10. As shown in FIG. 10, user interface 90 provides a display in which the user can view and modify the threshold level for a selected inspection process or a selected test of an inspection process and view the effect of changes to the threshold level on the success rate of the threshold level for detecting defects. User interface 90 includes Test drop down menu 92, which provides a method of switching between different tests performed in an inspection process. Changing the test, results in changes to the user interface such that the data collected for that particular test is displayed. For example, the user interface shown in FIG. 10 illustrates the data collected for test 3, while the user interface shown in FIG. 11 illustrates the data collected for test 1.

Additional information about the selected test may be illustrated in the user interface. For example, as shown below Test drop down menu 92, threshold type 94 that was used in the test may be illustrated. In the examples shown in FIGS. 10 and 11, the threshold type is SAT. However, the threshold type for which parameters may selected as described herein may include any other type of threshold known in the art such as, but not limited to, HLAT and XLAT. As further shown in the examples of FIGS. 10 and 11, box 96 may be selected if a nuisance filter is used in the test. The type of nuisance filter used in the test may be listed next to box 96. Although in the examples shown in FIGS. 10 and 11, only one possible nuisance filter (WISE-NF) is illustrated for the different tests, it is to be understood that any type of nuisance filters may be used with the tests. One or more parameters of the nuisance filter may be selected as described further herein.

Figure 11:
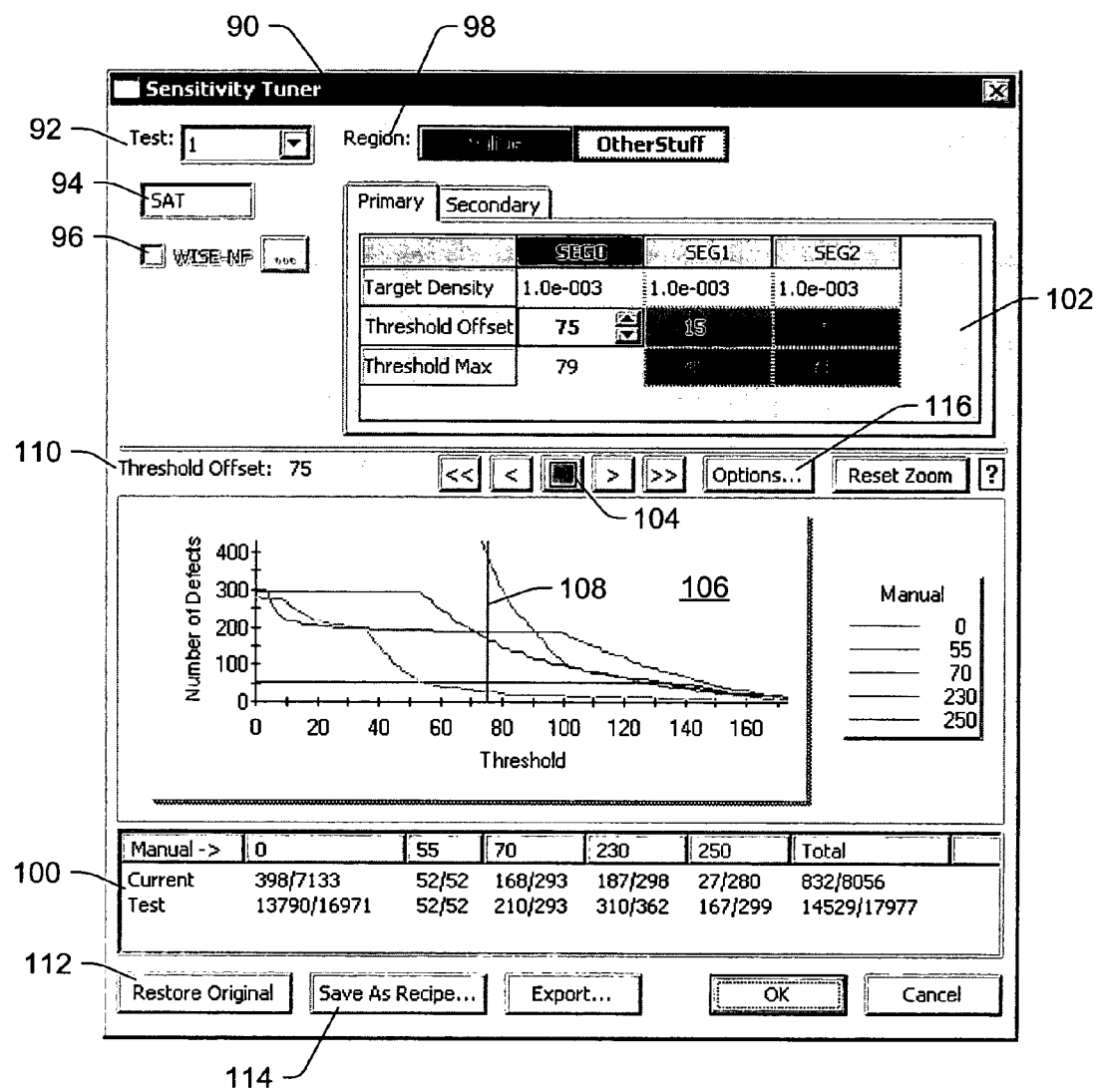

As further shown in FIGS. 10 and 11, Region option 98 controls the different regions displayed for the test. The user may click on one of the region boxes to display the information for that particular region. The user interface may display the status of updates to a threshold with different indicators such as color. The indicators may be used to denote if the threshold value has not been modified or viewed by the user, the threshold value has been modified by the user but the changes have not been updated to the inspection process recipe, or the threshold value has been updated to the inspection process recipe by the user.

Class code summary list grid 100 displays information about the number of defects detected with the currently selected threshold level and the total number of defects detected in the test. In particular, grid 100 has two rows, the Current row displays the number of defects caught per region with the current threshold level. The Test row displays the number of defects caught for the test as a whole. The rows display values in the format of Number of Defects caught/ Total number of defects. The user may also right click on the class code summary list grid to bring up a context menu (not shown) from which the user can select other class codes. In this manner, the information provided in grid 100 can be used to determine the threshold level that detects the most number of defects of a particular classification.

This process of sensitivity tuning is facilitated by having a relatively large number of defects classified that represent DOI, other real defects, defects that are not important, and nuisance events. In particular, it is useful to have a large number of all of these defect types classified across the operating curve of the parameter being tuned. In order to create this large classified defect set, the later described methods for 'Defects Like Me' and 'Diversity Sampling' are useful.

To change the threshold values, the user may click on the value to be changed in threshold table 102 located above the graph in the user interface. The threshold table may be configured such that the user may enter the new threshold value in any manner such as by direct input or by using a spinner. When the existing threshold value has been changed, the threshold table may indicate the change, for example, by changing the background color of the cell in which the altered threshold value is located. Button 104 can be selected to update the new threshold value to the recipe for the inspection process. Upon updating of the threshold value in the inspection process recipe, the threshold table may indicate the updating, for example, by again changing the background color of the cell in which the altered threshold value is located. Alternatively, changes to the threshold value may be made by using graph 106, which illustrates the number of different types of defects that are detected using various values for the threshold. For example, the user may move threshold value bar 108 on the graph to change the threshold value. The graph may be generated automatically by the computer-implemented method.

Tool bar 110 located above graph 106 provide tools to navigate between fields in the user interface. For example, the buttons marked with arrowheads may be used to move between fields. In addition, the Threshold Offset displayed in tool bar 110 displays the current threshold value selected in graph 106. The Reset Zoom button located in tool bar 110 resets the zoom value to a predetermined zoom value such as 100%.

User interface 90 may also include a number of additional options such as Restore Original button 112 shown below grid 100. Upon selection of Restore Original button 112, the original threshold parameters and nuisance filter values from the recipe will be restored. All of the status indicators in the user interface may also be restored. In addition, Save As Recipe button 114 is shown in the user interface below grid 100, which may be selected to save the current threshold level changes as a new recipe for the inspection system. Alternatively, the current threshold level changes may be written into an existing recipe for the inspection system. The user interface may also display Options button 116 above graph 106 in tool bar 110. Selection of Options button 116 brings up a dialog box (not shown) in which the user can limit the display of the defects. For example, the dialog box may include a current parameter's defects option, which may be selected to limit the graph to the defects that are caught using the current threshold parameter values. The dialog box may also include a current test's defects option that may be selected to limit the graph to the number of defects caught by the current selected test.

Figure 12:
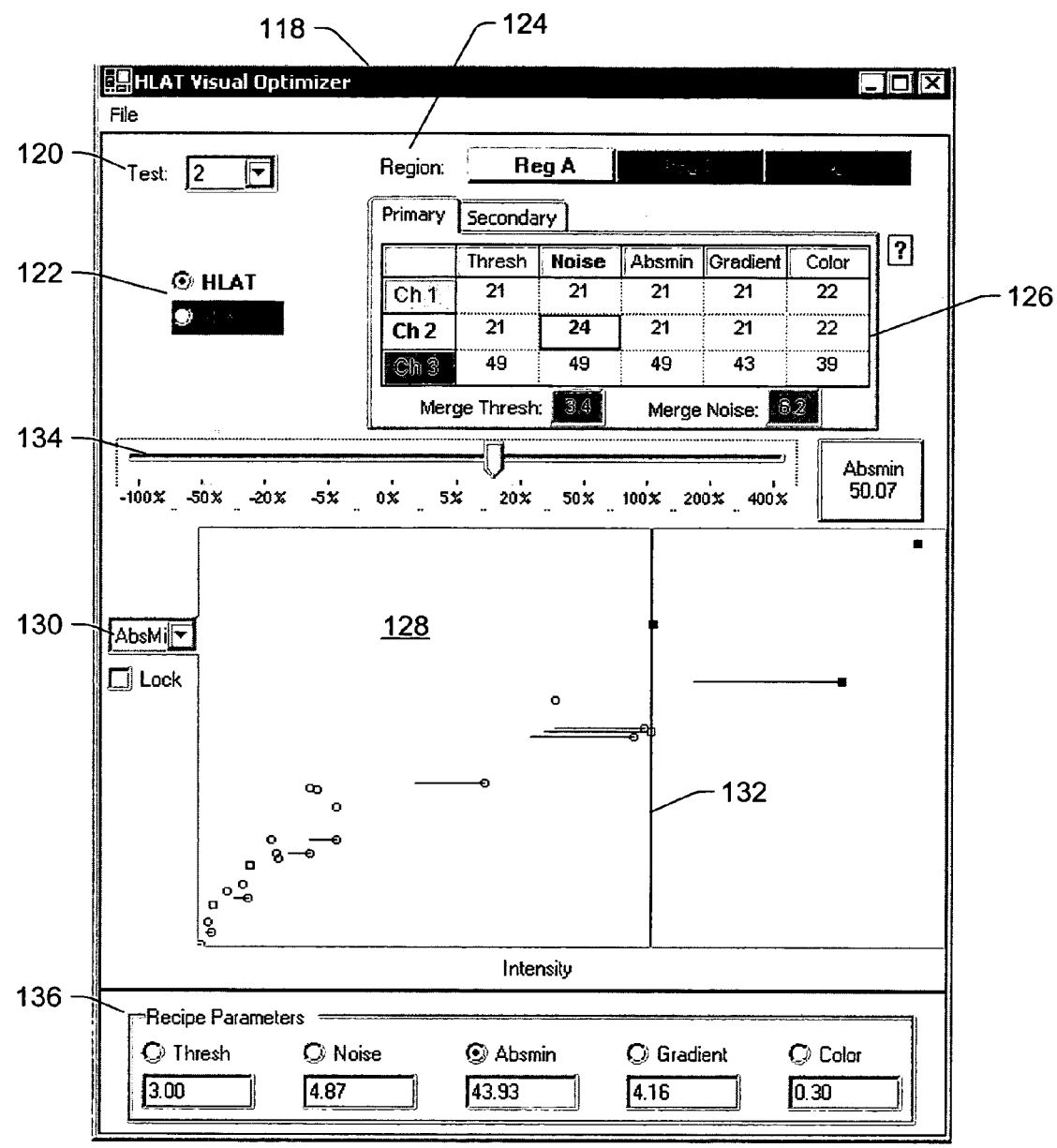

FIG. 12 illustrates a screenshot of another user interface that can be used to display and select parameter(s) of the sensitivity. As shown in FIG. 12, user interface 118 provides a display in which the user can view and modify the threshold level for a selected inspection process or a selected test of an inspection process and view the effect of changes to the threshold level on the success rate of the threshold level for detecting defects. User interface 118 includes Test drop down menu 120, which provides a method of switching between different tests performed in an inspection process. Changing the test, results in changes to the user interface to display the data collected for that particular test. For example, the user interface shown in FIG. 12 illustrates the data collected for test 2.

Like the user interfaces shown in FIGS. 10 and 11, the content and options displayed in the user interface of FIG. 12 depend on the test that is selected by the user. The user interface of FIG. 12 illustrates threshold type 122 for the test, which in this example, includes threshold types HLAT and XLAT. The user may select the type of threshold to be used for the test. As further shown in FIG. 12, Region option 124 controls the different regions displayed for the test. The user may click on one of the region boxes to display the information for that particular region. The user interface may display the status of updates to a threshold with different indicators such as color as described above.

To change the threshold parameters, the user may click on the value to be changed in threshold table 126. The threshold table may be configured such that the user may enter the new threshold value in any manner such as by direct input or by using a spinner. As shown in FIG. 12, the threshold table illustrates the five different parameters of HLAT, which include, from left to right in the threshold table, threshold, noise, absolute minimum for a characteristic of the defects (e.g., intensity), gradient, and color. The five different parameters are also illustrated in the threshold table for the different channels of the inspection system. In this manner, the user may select values for the five different parameters used for data generated by each of the channels separately.

Alternatively, changes to the threshold value may be made by using graph 128, which illustrates the characteristics of defects for different values of one of the threshold parameters. As shown in FIG. 12, the user may select the parameter for which the graph is shown from parameter drop down menu 130. The graph may be generated automatically upon selection of the parameter by the computer-implemented method. The user may select the value of the parameter to be used in the inspection process by moving bar 132 on the graph. Alternatively, the user may change the value of the selected parameter by moving slider 134 located above the graph. In addition, Recipe Parameters 136 located below the graph may indicate the current values of the threshold parameters for the test.

Even after sensitivity training, the results of the inspection process may still be relatively noisy and may contain nuisance events such as artifacts of the fabrication processes that do not affect yield. If this noise is present in the inspection process results, noise and/or nuisance removal may be performed. In the current technology, there are several methods for eliminating nuisance events such as WISE-NF, iADC-based NEF, which is also known as iNEF, and rule based binning, all of which are commercially available from KLA-Tencor. In addition, iADC may be used for binning the defects into one or more rough bins.

In some embodiments, the method may include selecting values for one or more parameters of a filter for the inspection process, as shown in step 138 of FIG. 1. The filter is configured to remove nuisance defects from the inspection data. One example of an appropriate filter for an inspection process is the WISE-NF filter described above. A nuisance filter may be configured to classify detected defects into nuisance defects or non-nuisance defects based on one or more characteristics of the defects. Defects identified as nuisance are then filtered out of the defect data.

Figure 13:
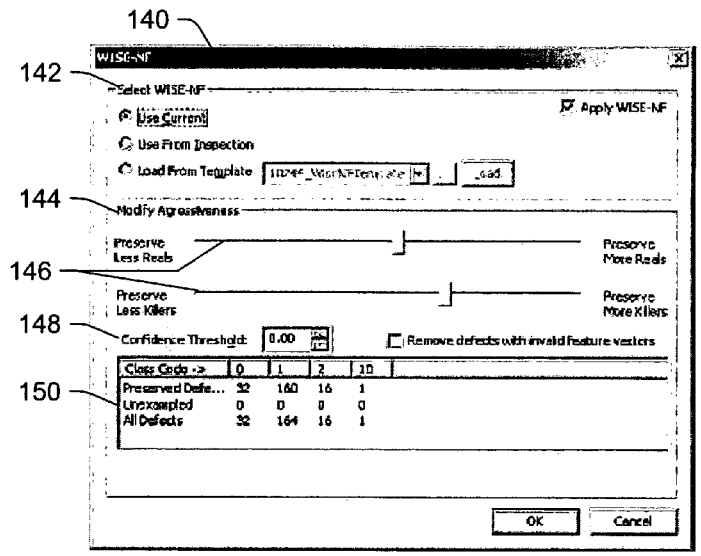
FIG. 13 is a screenshot illustrating one example of a user interface that can be used to select one or more parameters of a filter for an inspection process.

FIG. 13 illustrates one example of a user interface that can be used to select one or more parameters of a nuisance filter. Although the user interface is configured for selecting one or more parameters of a WISE-NF filter, it is to be understood that a similar user interface may be used to select one or more parameters of other nuisance filters with appropriate changes depending on the configuration of the nuisance filter. As shown in FIG. 13, user interface 140 provides the user with different choices for selecting and modifying parameter(s) of the filter. Select WISE-NF option 142 in user interface 140 provides the user with various options for the WISE-NF nuisance filter. The options include Use Current, which can be selected such that the values of the parameters as currently defined in the user interface are used for the inspection process. The options also include Use From Inspection, which can be selected such that the nuisance filter as defined in the inspection process is used. In addition, options 142 include Load From Template option, which the user can select to load a pre-defined nuisance template. The user may select the template in any manner known in the art. After the template has been chosen, the user may select the Load button.

User interface 140 also includes Modify Aggressiveness option 144, which provides controls to change the nuisance filter's ability to catch nuisance defects. In general, nuisance filters record what real and nuisance defects look like in terms of a probability distribution of their feature vectors. When evaluating a defect, if the feature vector of the defect falls within the recorded distribution of real or nuisance type, then the defect is classified as such. If not, the defect is considered as an unexampled defect.

Controls provided in the Modify Aggressiveness option include slider bars 146 and Confidence Threshold 148 parameter setting. The slider bars may be clicked and dragged to the desired level of aggressiveness for the filter. The results of the changes to the aggressiveness can be observed in defect information grid 150, which illustrates the defect counts and the distribution of different classes of defects (as indicated by the Class Codes across the top of the grid) in categories including Preserved Defects, Unexampled, and All Defects. The Confidence Threshold can be used to adjust the threshold value for unexampled defects (i.e., defects that have not been classified as either nuisance or real). In particular, the Confidence Threshold specifies how much confidence the WISE-NF must have to determine that a defect is either a real or nuisance defect type. The Confidence Threshold is expressed in terms of a probability measure. The range of the Confidence Threshold control can be 0-32. Setting a higher value for the Confidence Threshold will result in more defects falling into the unexampled defect category. On the contrary, if the Confidence Threshold value is 0, then no defects will be placed in the unexampled category.

In current implementations of tuning thresholds, the user is able to separate defects using purely appearance-based features in an algorithm called "Unsupervised Grouping" or "Natural Grouping." This implementation is an alternative to performing full manual classification of defects before tuning the sensitivity. However, the methods described herein may use a binning process such as one of those described in co-pending, commonly assigned U.S. Patent Application Ser. No. 60/618,475 to Teh et al. filed on Oct. 12, 2004, which is incorporated by reference as if fully set forth herein. Instead of simply using appearance-based features of the defects for binning, the methods described in this patent application use additional information about the defects for binning. For example, these methods include applying a sequence of rules for defects to inspection data generated by inspection of a semiconductor specimen. The sequence of rules includes statistical rules, deterministic rules, hybrid statistical and deterministic rules, or some combination thereof. Therefore, the methods described by Teh et al. provide better separation of the defects.

Just as better separation of the defects is more valuable for finding defects of interest as further described herein, better separation during tuning will result in better recipe tuning. In the methods described herein, the user can utilize any of the various binning methods described by Teh et al. or create new binning methods to feed into the defects bins used in threshold tuning.

In additional embodiments, the method may include selecting one or more parameters of a binning process to be used with the inspection process, as shown in step 152 of FIG. 1. In one embodiment, the method may include performing the inspection process on the specimen to generate additional inspection data, as shown in step 154. This step may be performed with any values of one or more parameters of the inspection process that have already been optimized as described herein. One such embodiment includes applying a sequence of rules for defects to the additional inspection data, as shown in step 156. The sequence of rules may include statistical rules, deterministic rules, hybrid statistical and deterministic rules, or some combination thereof. In addition, such an embodiment may include classifying the defects based on results of the application of the sequence of rules, as shown in step 158.

This embodiment of the method further includes tuning a threshold value or another parameter of the inspection process based on results of the classification step, as shown in step 160. In addition, one or more other parameters of the sensitivity and/or one or more parameters of the filter may be altered based on the results of the classification step. One or more parameters of the binning process to be used with the inspection process may also be selected and optimized in this manner. In one embodiment of this embodiment, steps 154, 156, 158, and 160 may be performed by the computer-implemented method without input from a user.

In some embodiments, applying the sequence of the rules, as shown in step 156, may be performed with different values for one or more parameters of at least one of the sequence of rules. This method includes classifying the defects based on results of the application of the sequence of rules, as shown in step 158. In addition, this method includes displaying results of the classification step, as shown in step 162, such that a user can select values for the one or more parameters to be used with the inspection process. The values that are selected for the parameter(s) to be used with the inspection process may include parameter(s) for the binning process, parameter(s) for the sensitivity, parameter(s) for the filter, etc.

In this manner, the method may be configured for user-assisted selection of the binning parameters. For example, the results displayed in step 162 may be displayed with a user interface configured such that the user interface may be automatically populated by the computer-implemented method based on one or more selections by the user. One possible user interface for selecting one or more parameters of a threshold provides feedback to a user on the operating curves produced from various system settings. Examples of operating curves are shown in FIGS. 10 and 11 in graph 106. This display technique may be used for tuning the binning recipe by providing feedback on the rule-based part of the binning method. The user can set more effective tolerances on the rules at each node one at a time by seeing the effect of the changes to the tolerances in the curve. In one embodiment, the process of setting up the parameters of the inspection process would be serial, with threshold information used to set the parameter(s) for binning. In a different embodiment, the parameters for the threshold and the binning can be performed together or iteratively.

In another embodiment, the method may include performing the inspection process two or more times on at least a portion of the specimen to produce two or more sets of additional inspection data, as shown in step 164 of FIG. 1. The inspection process that is used in this step may be performed with values of the image acquisition parameter(s) that have been selected and/or optimized as described above if the optimization of the image acquisition parameter(s) has been performed. This embodiment also includes identifying defects that appear in a number of the two or more sets that is less than a predetermined number as nuisance defects, as shown in step 166. One such embodiment may also include tuning a threshold for the inspection process based on results of the identifying step, as shown in step 168.

The above embodiment for tuning a sensitivity parameter may be used, for example, in cases in which the technology is well understood such as at a foundry producing many different devices using similar processing techniques. In this case, the customer is primarily interested in reducing the number of nuisance events to a known tolerance. For this case, the method for determining the acceptable nuisance level includes first running an inspection with a "hot" recipe a number of times. A hot recipe is an inspection recipe in which defect detection is performed with an extremely low threshold (e.g., much lower than will actually be used for the inspection process) without filtering such that the largest possible defect population can be detected. A matching process may be performed on the detection results to identify the defects that are found at an acceptable predetermined repeatability. Any matching process known in the art such as CapRate, MatchApp, and defect source analysis (DSA) may be used in this step. The defects that occur less frequently may be identified as noise or nuisance defects.

In a particular example, assume that the user wants a relatively high level of confidence (e.g., 75% confidence) that events are real. The user could run the inspection over a relatively small area of a specimen multiple times (e.g., 8 times), and then eliminate events that were caught fewer than six times out of the eight. In another example, the user could run the inspection the same number of times (e.g., 8 times), but accept a result that is lower. In the easiest case, the user could run the inspection process twice and set the standard that defects that were not caught in both runs should be eliminated. This filtering can be fed into the threshold tuning algorithm described above instead of using a classification or binning methodology. Although this technique for threshold tuning can be performed manually using off-line tools such as MatchApp and Klarity to determine the real and nuisance defects, obviously, it would be advantageous to perform this threshold tuning technique automatically using the computer-implemented methods described herein.

Obviously, the first hurdle in setting up an inspection recipe is to find the DOI or the selected defect described above. Until finding the selected defect has been performed, there is no reason to believe that the recipe can be effective. Finding the DOI has been likened to finding a needle in a haystack. The search for the DOI is particularly difficult if it is performed with a SEM since several visits may be required to accomplish the work. One important recent change to inspection system technology is that inspection and/or review systems can access inspection information generated by another inspection system and may have the same tools available as the other inspection system. In this manner, the search for the DOI may be completed in one visit. However, this breakthrough in technology may be further enhanced through the DOI finding methods described herein.

One method for finding the DOI includes performing multiple inspection processes using many different modes and thresholds to find all of the possible defects on the specimen. From this large population, pruning techniques are used to get the data set down to a reasonable beginning defect population. On the 23xx tool that is commercially available from KLA-Tencor, this pruning may be performed by running an inspection in a multiple test mode and applying a function to the inspection data using a user interface having Test/Union/Difference functionality.

The DOI finders described herein have two major components, which are referred to herein as "Diversity Sampling" and "Defects Like Me." In one embodiment, the method includes generating initial inspection data for the specimen with the inspection system, as shown in step 170 of FIG. 1. This embodiment also includes identifying the selected defect in the initial inspection data, as shown in step 172. In one embodiment, identifying the selected defect includes detecting multiple defects on the specimen having the greatest diversity of one or more characteristics of the multiple defects.

In one particular example, the Diversity Sampling technique makes use of all available information about the defects such as attributes, location, background, and appearance to find the most diverse set of defects possible. In one embodiment, the system will control all attributes used in the Diversity Sampling algorithm. In another embodiment, the user may control some or all of the attributes used for Diversity Sampling. The user can visit these sampled defects singly under review conditions or view them in a gallery to locate the DOI. Controlling the attributes used in the Diversity Sampling algorithm may be particularly valuable when a "hot" recipe is run since the results of such an inspection process may include a population of defects, of which the vast majority are nuisance events and the DOI make up a relatively small minority of the population. As such, standard sampling may be ineffective for finding the DOI in such inspection results.

Figure 14:
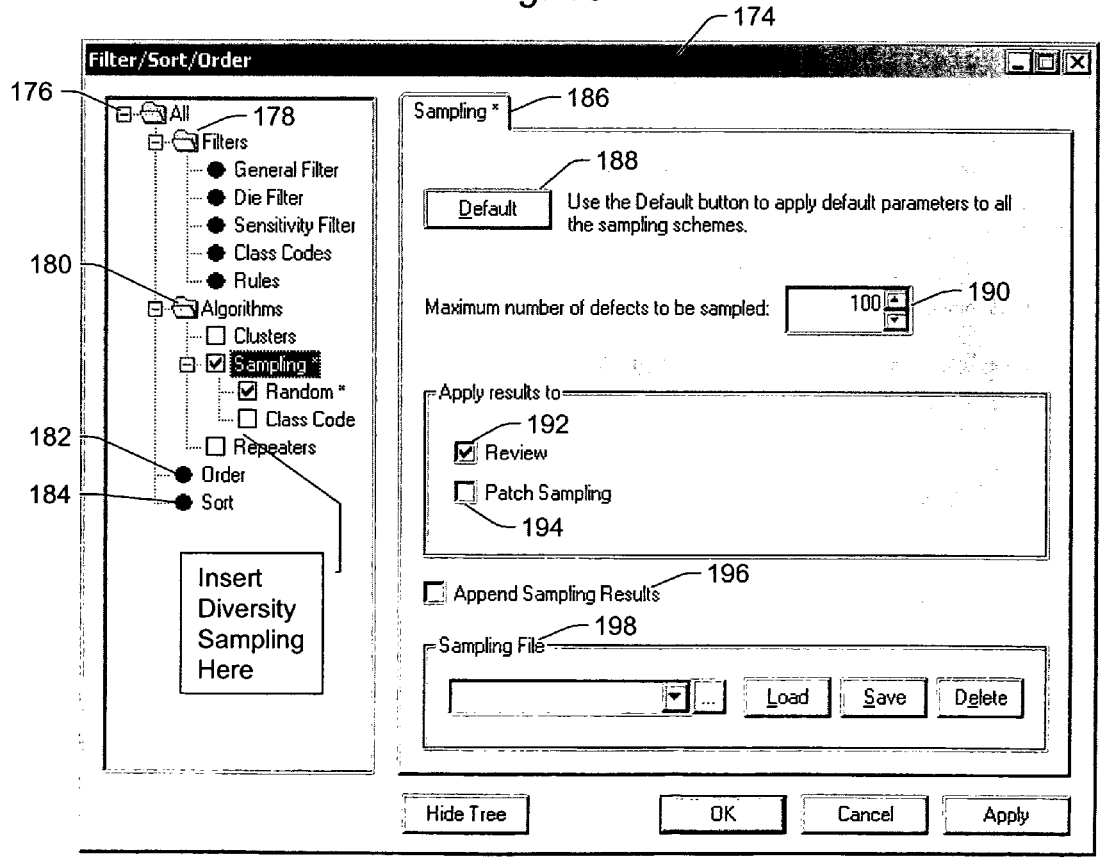
FIGS. 14-20 are screenshots illustrating examples of different user interfaces that can be used to identify one or more selected defects in initial inspection data generated for a specimen with an inspection system.

FIG. 14 illustrates a currently used user interface into which the Diversity Sampling option may be inserted. In particular, user interface 174 may be configured for sampling of defects during review. As shown in FIG. 14, the user interface includes tree 176 illustrating options for filters and algorithms to be applied to the inspection data for sampling. Filter options 178 include, in this example, a General Filter, a Die Filter, a Sensitivity Filter, Class Codes, and Rules. These filters may be configured as described herein. In addition, the filter options may include fewer than these filter examples as well as any other filters known in the art. The user may select one or more of the filters by clicking on the circle next to the filter. For example, as shown in FIG. 14, all of the available filters have been selected by the user.

Algorithms options 180 include Clusters algorithm and Sampling algorithms, which include Random sampling and Class Code sampling, which may have any configuration known in the art. In addition, in one embodiment, user interface 174 may be modified to include a Diverse Sampling algorithm as shown in FIG. 14, which may be performed as described above. User interface 174 also includes Order option 182 and Sort option 184, which may be used to arrange the defects in a meaningful manner. Ordering and sorting of the defect population may be performed after filtering and application of the selected algorithms. In addition, ordering and sorting of the defect population may be performed in any manner known in the art.

As further shown in FIG. 14, user interface 174 includes options for sampling of the defect population. For example, Sampling tab 186 includes Default button 188, which may be used to apply default parameters to all of the sampling schemes. In addition, option 190 allows the user to select the maximum number of defects that are to be sampled. The user interface also allows the user to select whether the results are applied to Review 192 and/or Patch Sampling 194. The user may also select Append Sampling Results option 196 and Sampling File 198 to which the results will be appended.

Figure 15:
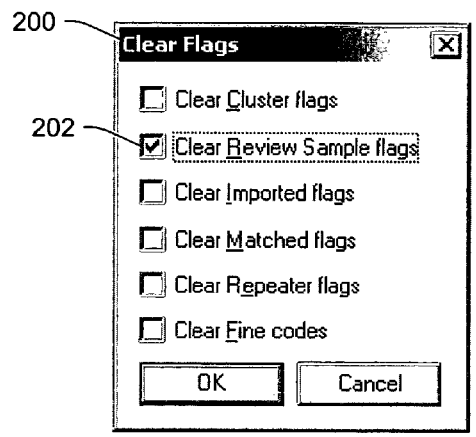

FIG. 15 illustrates user interface 200 in which the user can select to exit out of diverse sampling in review by clearing flags. In particular, the user can select Clear Review Sample flags option 202 to clear flags for diverse sampling.

Figure 16:
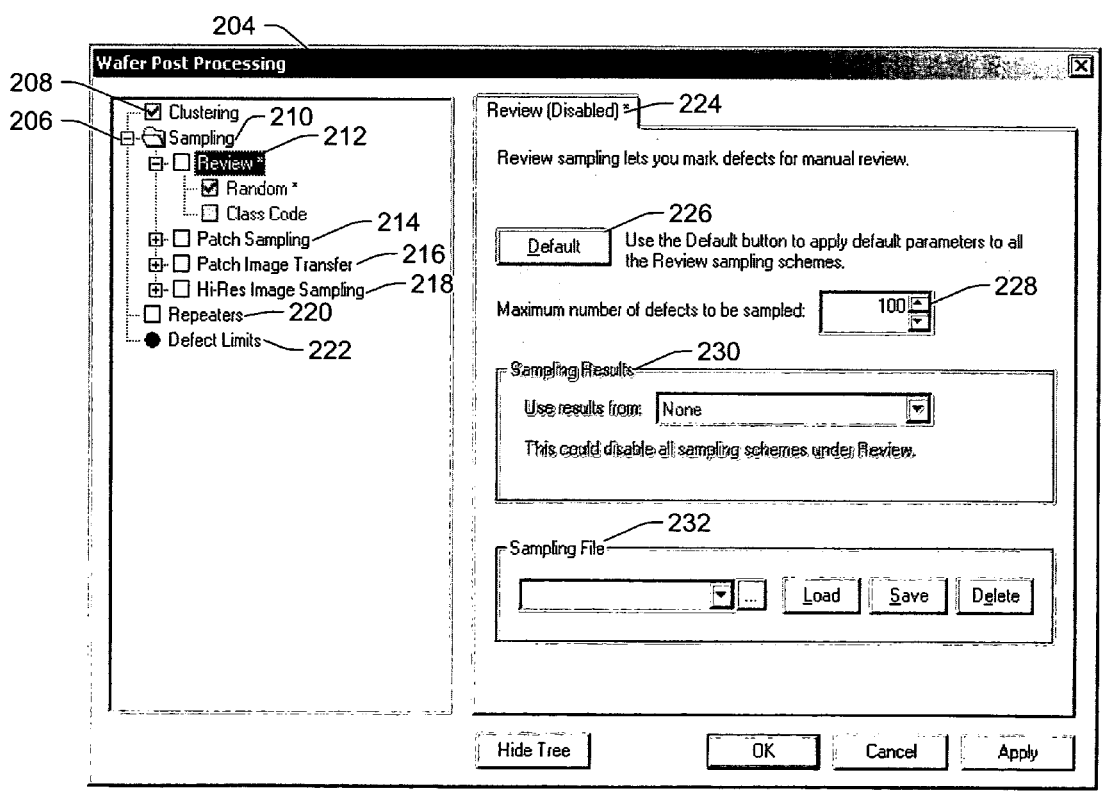

FIG. 16 illustrates a user interface that can be used to set up the Diversity Sampling from a run. In particular, FIG. 16 illustrates Wafer Post Processing user interface 204 in which tree 206 illustrates a number of options for the user. In particular, tree 206 includes Clustering option 208, which the user can select to analyze the defect population for clusters of individual defects that may actually be part of a single larger defect. In addition, tree 206 includes Sampling option 210. Sampling option 210 illustrates a number of different options including Review option 212, which allows the user to indicate the defects for manual review. Review option 212 may also include a number of different sampling options such as Random, Class Code, and Diversity Sampling (not shown). The Sampling options may also include Patch Sampling option 214, Patch Image Transfer 216, and Hi-Res (high-resolution) Image Sampling 218, all of which indicate the type of images that will be used to sample the defects. Tree 206 also includes Repeaters option 220, which the user may select to have the defect population analyzed for repeating defects. In addition, tree 206 also includes Defect Limits option 222, which the user can select to use limits in selecting defects for review.

User interface 204 may also include Review tab 224. Review tab 224 may be enabled when Review option 212 is selected. Review tab 224 includes Default option 226, which the user can select to apply default parameters to all of the Review sampling schemes. In addition, the Review tab includes option 228, which allows the user to select the maximum number of defects that are to be sampled. The Review tab also includes Sampling Results option 230, which may be used to select results that are to be used for review. Selection of particular results for review could disable all of the sampling schemes under Review. User interface 204 also includes Sampling File option 232, which allows the user to Load, Save, or Delete a particular sampling file.

In a different embodiment, identifying the selected defect in the initial inspection data, as shown in step 172 of FIG. 1, may include identifying a plurality of the selected defects in the initial inspection data, which may include locating a first of the selected defects and searching for a second of the selected defects based on the initial inspection data associated with the first of the selected defects. Therefore, this method for finding DOIs may be referred to as "Defects Like Me." In one such embodiment, the computer-implemented may use an algorithm that is configured to find similar defects in a defect population, and the user may control the factors that are used to determine if defects are similar.

This embodiment for locating similar defects in a defect population may use all of the knowable information about the defects in a meaningful order such as that described in the patent application by Teh et al., which is incorporated by reference above. Identifying multiple DOI that are similar may be an important step in the setting up of an inspection process because once a single instance of a DOI has been located, the next step is to find more defects. In this manner, the imaging conditions of the recipe can be tuned using multiple DOI so that the inspection process can detect more examples of the DOI under all conditions on the wafer. To return to the haystack analogy, once the first needle is found, the user wants to find more needles.

Another usage of "Defects Like Me" in finding the DOI is to identify the noise and nuisance events more quickly. In addition, as irrelevant defects are found, the user may prefer to eliminate these defects quickly. For instance, after the algorithm finds similar events identified as noise or nuisance events, the user may "zap" or eliminate all of the noise or nuisance events in one stroke. In the haystack analogy, this elimination of the noise or nuisance events is equivalent to reducing the haystack without losing the needles.

The Defects Like Me step used in the computer-implemented method may be performed as a user-assisted step. For instance, the user may select one or more parameters of the Defects Like Me step. Such parameters include, but are not limited to: controlling the number of defects in each similar bin; controlling the confidence level in separating defects; controlling the defect attribute groups and feature groups used in performing the binning; allowing context/reference features to be used in performing the separation (e.g., to identify defects in similar/different environments); setting weights on the groups; setting the threshold for rules used to separate defects; sorting the defects using criteria to make the search faster; feedback to the user on the ranking of the feature groups in performing the separation; and feedback on the ways in which defects are similar or different. It is to be understood that the computer-implemented method may be configured to allow the user to select one or more of the these parameters (i.e., any combination of these parameters) for the Defects Like Me step. Some examples of user interfaces that may be used to allow the user to select some of these parameters are described below.

Alternatively, the Defects Like Me step may be performed entirely by the computer-implemented method (i.e., without input from the user). In this manner, the computer-implemented method may be configured to determine appropriate values for the parameters of the Defects Like Me step based on, for instance, characteristics of the selected defect and/or characteristics of the specimen. In addition, the computer-implemented method may be configured to adjust the values for the parameters of the Defects Like Me step in real time (i.e., as the similar defects are found) based on, for example, characteristics of the defects determined to be similar.

Figure 17:
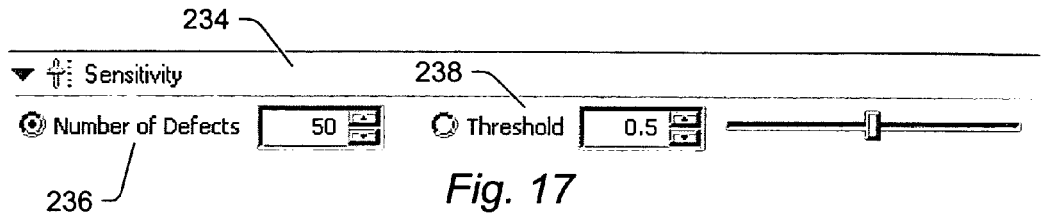

FIG. 17 illustrates one user interface that is configured to allow the user to set the number of defects and the confidence level for Defects Like Me. In particular, user interface 234 includes Number of Defects option 236. By selecting the Number of Defects option, the user can select the number of defects to be searched for based on the characteristics of a single selected defect. The user may set the Number of Defects by direct input or by using the spinner shown in FIG. 17. In addition, user interface 234 includes Threshold option 238, which the user can select to set the threshold used to determine if two defects are similar enough to be considered the same type of defect. In this manner, a lower threshold value will result in more defects being qualified as similar, and a higher threshold value will result in fewer defects being qualified as similar, possibly with fewer errors. The user may select the threshold value by direct input, by using the spinner, or by using the slider shown in FIG. 17.

Figure 18:
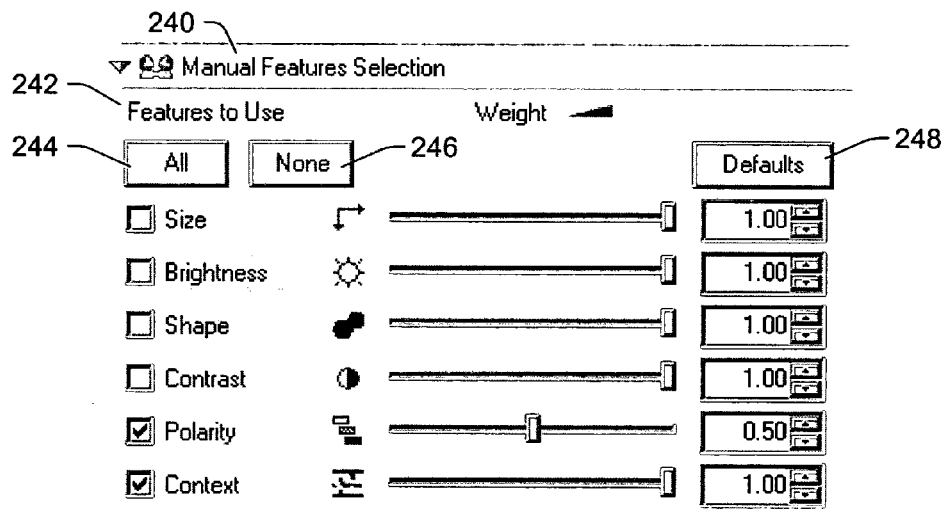

FIG. 18 illustrates a user interface that is configured to allow a user to control the binning groups and their weighting for an example tool. In particular, user interface 240 includes Features to Use option 242. As shown in FIG. 18, the user may select All button 244 to select all of the features illustrated in the user interface. Alternatively, the user may select None button 246 to select none of the features illustrated in the user interface. The Features to Use option includes a number of different features that may also be selected individually, in any combination, for use in binning. The different features include Size, Brightness, Shape, Contrast, Polarity, and Context. Obviously, the different features may include any other features that can be measured by the inspection system. In addition, the different features may include fewer than the features shown in FIG. 18.

The user may select the different features to be used for binning individually by clicking on the box next to each feature name. In addition, the user may select a weighting for each of the different features individually. The weighting may be selected for the different features using the slider located next to the name of each individual feature, by direct input in the input box located in the same row as each feature name, or by using the spinner shown next to the input box. Alternatively, the user may elect to use the default weights for each of the selected different features by selecting Defaults button 248.

Figure 19:
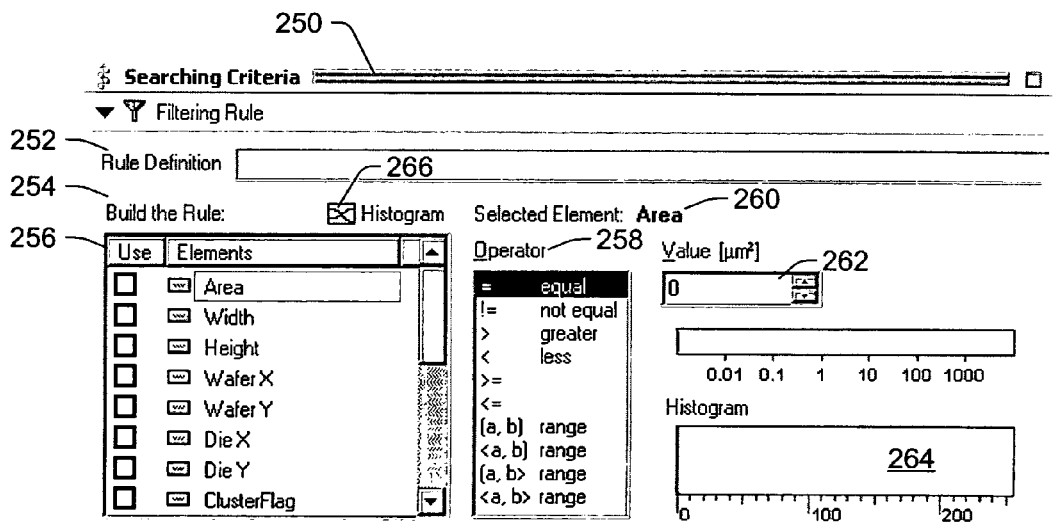

FIG. 19 illustrates one example of a user interface that is configured to allow the user to select rules to be used along with the binning groups for the binning step. As shown in FIG. 19, user interface 250 includes Rule Definition 252, which may display a description of a rule. The description of the rule may be input by the user. Alternatively, the description of the rule may be generated by the computer-implemented method as the rule is being generated. User interface 250 also includes Build the Rule section 254 in which the user may select one or more parameters of the rules to be used with binning. Build the Rule section 254 includes list 256 of a number of different elements that can be selected or de-selected by a user for use in the rule by clicking on the box shown next to the name of each element. As shown in FIG. 19, the elements may include, but are not limited to, Area, Width, Height, Wafer X, Wafer Y, Die X, Die Y, and Cluster Flag. The user may select one or more of the elements for use in the rule.

Build the rule section 254 includes Operator list 258 of possible operators that may be combined with the selected element. In this manner, the method may include building one or more of the rules included in a sequence by applying unrestricted Boolean operators to defect elements. The list of possible operators may be altered depending on which element is selected by the user. If more than one element is selected to be used in a rule, the operators to be used with each element may be determined independently by first selecting one of the element names and selecting the operators and other variables described herein for this element. For example, as shown in FIG. 19, Area was selected as shown by the highlighted name of the element and Selected Element indicator 260 such that the parameters for the area element can be selected. Then, a different element may be selected, and the parameters for that element may be selected in the same manner until all of the parameters for the selected elements have been chosen.

The Build the Rule section further includes Value input 262 in which a user can select a value to be used with the selected operator. The user can enter the value by direct input or by using the spinner shown next to the input box. The Build the Rule section may also display histogram 264 if histogram option 266 is selected. The histogram may illustrate the number of defects that have various values of the selected element. In this manner, the Build the Rule section may provide information about the defects to the user such that the user can use this information to build a rule that will be useful for the defects on the specimen.

Figure 20:
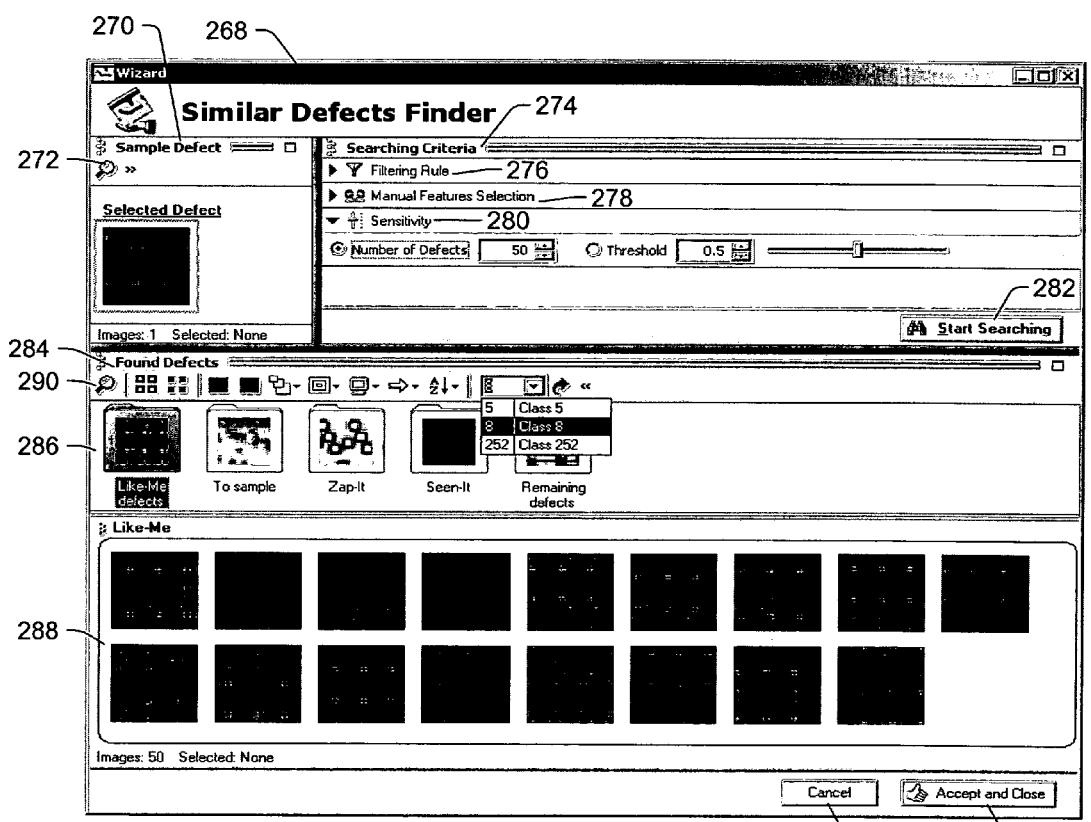

FIG. 20 illustrates one example of a user interface that is configured for viewing the results of the Defects Like Me step. As shown in FIG. 20, user interface 268 includes Sample Defect box 270, which illustrates the defect that is selected by the user. In particular, the Sample Defect box in this example illustrates the patch image of the defect. However, any other information about the selected defect may be illustrated in the Sample Defect box. As also shown in FIG. 20, the user may perform one or more functions on the image of the selected defect using icons in tool bar 272.

The user interface also includes Searching Criteria box 274, in which the user can select one or more parameters for searching for defects that are similar to the selected defect. In particular, Searching Criteria box 274 includes Filtering Rule option 276, which when selected may result in the user interface shown in FIG. 19 being displayed. In addition, Searching Criteria box 274 includes Manual Features Selection option 278, which when selected may result in the user interface shown in FIG. 18 being displayed. Searching Criteria box 274 also includes Sensitivity option 280, which when selected (as shown in FIG. 20) may result in the user interface shown in FIG. 17 being displayed in Searching Criteria box 274.

Searching Criteria box 274 also includes Start Searching button 282, which the user can click after the appropriate choices have been made in the Searching Criteria box. During or after searching, images of the defects that are determined to be like the selected defect based on the searching criteria may be illustrated in Found Defects section 284 of the user interface. In particular, the searching results may be displayed as a plurality of folders 286 into which similar defects have been placed. For example, individual defects may be placed into folders for Like Me defects, To sample defects, Zap-It defects, Seen-It defects, and Remaining defects. The Like Me defects folder includes the defects which are similar to the selected defect. The To sample defects folder includes defects that have been identified as possible candidates for sampling during review. The Zap-It defects folder includes those defects that may be noise or nuisance defects and as such are slated for removal from the defect population. The Seen-It defects folder includes non-noise or non-nuisance defects (i.e., real defects) that are not similar to the selected defect. The Remaining defects folder includes defects that are unexampled or unknown defects.

As shown in FIG. 20, the user interface may illustrate a defect image on the front of each folder that is representative of the defects in the particular folder. In this manner, the defects in each folder may be quickly compared by the user. In addition, the user interface allows the user to view the defects within each group. For example, by selecting one of the folders (in this case, the Like Me defects folder is selected), the defect images within that folder are illustrated in window 288. In this manner, the user may evaluate the results of the Defects Like Me step. In addition, as shown in FIG. 20, the user may perform a number of different functions on the defect images using icons in tool bar 290. The user may also select to accept the found defects using Accept and Close button 292. Alternatively, the user may decide to quit the Defects Like Me function using Cancel button 294.

Figure 21:
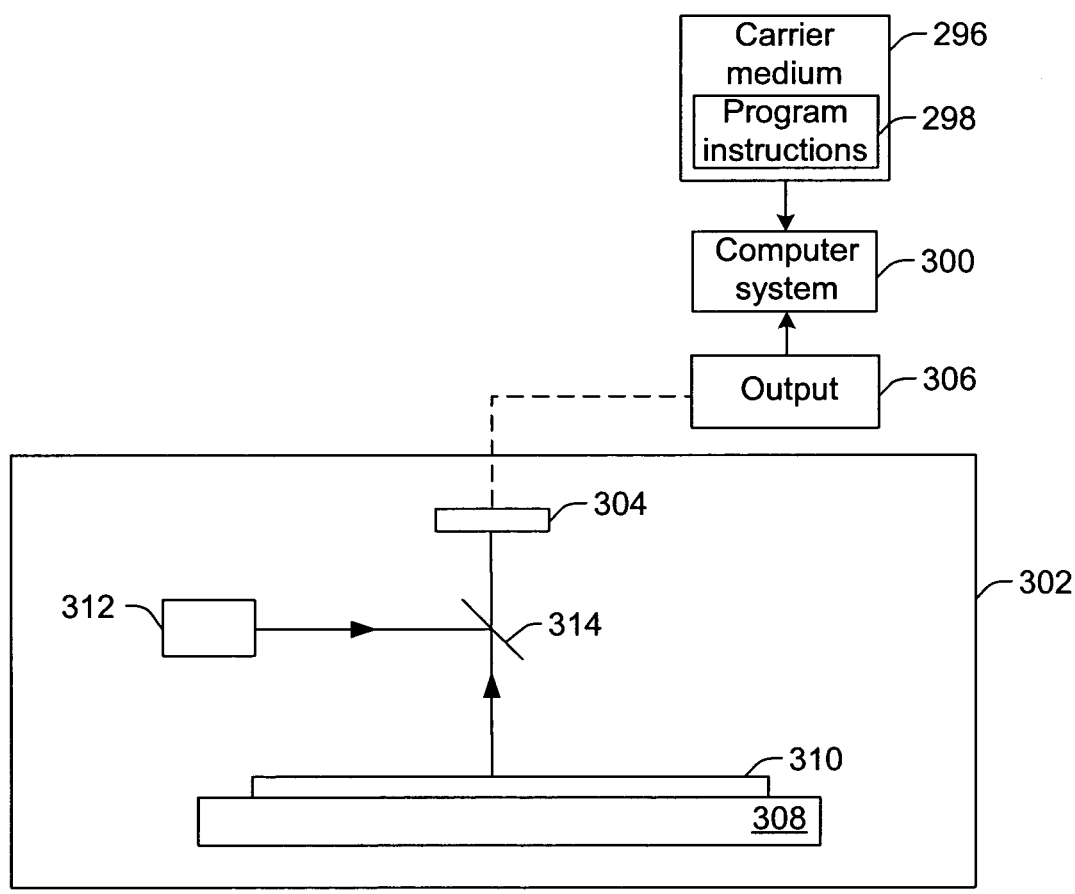
FIG. 21 is a schematic diagram illustrating a side view of one embodiment of a system that is configured to generate an inspection process.

Another embodiment relates to carrier medium 296 as shown in FIG. 21. Carrier medium 296 includes program instructions 298 executable on computer system 300 for performing a method for generating an inspection process for an inspection system. The method includes generating data for a specimen at different values of one or more parameters of the inspection system, which may be performed, for example, as shown in step 10 of FIG. 1. The one or more parameters include one or more image acquisition parameters, one or more sensitivity parameters, or some combination thereof. The method also includes determining which of the different values produces the best data for the specimen, which may be performed, for example, as shown in step 56 of FIG. 1. In addition, the method includes selecting the different values determined to produce the best data as values of the one or more parameters to be used for the inspection process, which may be performed, for example, as shown in step 58 of FIG. 1. The method for which the program instructions are executable may include any other step(s) described herein.

Program instructions implementing methods such as those described herein may be transmitted over or stored on the carrier medium. The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

The computer system may take various forms, including a personal computer system, mainframe computer system, workstation, image computer or any other device known in the art. In general, the term "computer system" may be broadly defined to encompass any device having one or more processors, which executes instructions from a memory medium.

FIG. 21 also illustrates one embodiment of a system that is configured to generate an inspection process for an inspection system. The system shown in FIG. 21 includes inspection system 302. Inspection system 302 is configured to generate data for a specimen at different values of one or more parameters of the inspection system. The one or more parameters include one or more image acquisition parameters, one or more sensitivity parameters, or some combination thereof. In the example shown in FIG. 21, the inspection system is configured to inspect a wafer. Although the inspection system is shown in FIG. 21 to be an optical based inspection system, it is to be understood that the inspection system shown in FIG. 21 may be configured to image the wafer in a different way. For example, the inspection system may be configured to inspect a wafer by imaging the wafer with electron beams (i.e., an electron beam based imaging system or SEM). In addition, the inspection system may be configured to inspect a specimen without imaging the specimen. Furthermore, the inspection system may be replaced with a review system (not shown). Alternatively, the system may include an inspection system and a review system.

Inspection system 302 is coupled to computer system 300. For example, one or more components of inspection system 302 may be coupled to computer system 300 by a transmission medium (not shown). The transmission medium may include "wired" and "wireless" portions. In another example, detector 304 of inspection system 302 may be configured to generate output 306. The output may be transmitted across a transmission medium from detector 304 to computer system 300. In some embodiments, the output may also be transmitted through one or more electronic components interposed between the detector and the processor. Therefore, output 306 is transmitted from the inspection system to the computer system.

Computer system 300 is configured to perform one or more steps of a computer-implemented method as described herein using the data of output 306. For example, the computer system is configured to determine which of the different values produces the best data for the specimen. The computer system is also configured to select the different values determined to produce the best data as values of the one or more parameters to be used for the inspection process. The computer system may also be configured to perform one or more other step(s) of any of the computer-implemented methods described herein (e.g., Diversity Sampling, Defects Like Me searching, etc.). The computer system may perform these and any other steps described herein using program instructions 298 included in carrier medium 296.

Inspection system 302 may be configured to inspect the specimen using any technique known in the art. In addition, the inspection system includes stage 308 upon which specimen 310 may be disposed during imaging or inspection. The stage may include any suitable mechanical or robotic assembly known in the art. The inspection system also includes light source 312. Light source 312 may include any appropriate light source known in the art. In addition, the inspection system may include beam splitter 314, which is configured to direct light from light source 312 onto specimen 310 at angles that are approximately normal to an upper surface of specimen 310. The beam splitter may include any suitable beam splitter known in the art. The inspection system further includes detector 304, which is configured to detect light transmitted by beam splitter 314. The detector is also configured to generate output 306. The detector may include any suitable detector known in the art.

Although one general configuration of the inspection system is shown in FIG. 21, it is to be understood that the inspection system may have any suitable configuration known in the art. For example, the inspection system may be configured to perform a single channel imaging technique as shown in FIG. 21. Alternatively, the inspection system may be configured to perform a multiple channel imaging technique. In addition, the optical inspection system may be replaced with an e-beam inspection tool such as a CD SEM and the eS25 and eS30 systems, which are commercially available from KLA-Tencor. Such an inspection system may be coupled to the computer system as described above.

Further modifications and alternative embodiments of various aspects of the invention may be apparent to those skilled in the art in view of this description. For example, methods and systems for generating an inspection process for an inspection system are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for generating an inspection process for an inspection system, comprising:
   generating initial inspection data for a specimen with the inspection system;
   Using a computer or processor to perform the method steps of:
   identifying a selected defect in the initial inspection data, wherein said identifying comprises detecting multiple defects on the specimen having the greatest diversity of one or more characteristics of the multiple defects;
   generating inspection data for the selected defect on the specimen at different values of one or more image acquisition parameters of the inspection system;
   determining which of the different values produces the best inspection data for the selected defect; and
   selecting the different values determined to produce the best inspection data as values of the one or more image acquisition parameters to be used for the inspection process.

2. The method of claim 1, further comprising identifying a plurality of the selected defects in the initial inspection data, wherein said identifying further comprises locating a first of the selected defects and searching for a second of the selected defects based on the initial inspection data associated with the first of the selected defects.

3. The method of claim 1, wherein the best inspection data comprises the inspection data having the highest signal-to-noise ratio for the selected defect or the best separation between the selected defect and noise in the inspection data.

4. The method of claim 1, wherein the different values correspond to one or more tests that can be performed on the specimen by the inspection system.

5. The method of claim 4, wherein the inspection process comprises the one or more tests.

6. The method of claim 1, wherein the values of the one or more image acquisition parameters to be used in the inspection process comprise values for two or more tests to be performed with different image acquisition modes in the inspection process.

7. The method of claim 1, further comprising identifying available options for the different values of the one or more image acquisition parameters and displaying the available options to a user for selection.

8. The method of claim 1, wherein the different values and the one or more image acquisition parameters are selected by a user for use in the inspection process.

9. The method of claim 1, wherein the different values and the one or more image acquisition parameters are selected without input from a user.

10. A computer-implemented method for generating an inspection process for an inspection system, comprising:
    generating data for a specimen at different values of one or more sensitivity parameters of the inspection process;
    displaying the data such that a user can select a value of the data;
    Using a computer or processor to perform the method steps of:
    selecting values of the one or more sensitivity parameters to be used for the inspection process based on the value of the data selected by the user;
    performing the inspection process two or more times on at least a portion of the specimen to produce two or more sets of additional inspection data; and
    identifying defects that appear in a number of the two or more sets that is less than a predetermined number as nuisance defects.

11. The method of claim 10, wherein said selecting is performed by the user with assistance from the computer-implemented method.

12. The method of claim 10, further comprising collecting statistics on performance of the one or more sensitivity parameters across multiple subdivisions of an inspected area on the specimen without any prior knowledge or assumption of initial values of the one or more sensitivity parameters.

13. The method of claim 12, further comprising automatically determining the initial values for the one or more sensitivity parameters based on the statistics, wherein the initial values are used to determine the different values of the one or more sensitivity parameters, and wherein said generating comprises detecting events in each of the multiple subdivisions.

14. The method of claim 12, further comprising displaying a summary of the statistics such that the user can select the initial values for the one or more sensitivity parameters.

15. The method of claim 12, further comprising automatically selecting the initial values for the one or more sensitivity parameters based on the statistics.

16. The method of claim 10, further comprising performing the inspection process on the specimen to generate additional inspection data, applying a sequence of rules for defects to the additional inspection data, classifying the defects based on results of said applying, and tuning a threshold value of the inspection process based on results of said classifying.

17. The method of claim 10, further comprising performing the inspection process on the specimen to generate additional inspection data, applying a sequence of rules for defects to the additional inspection data with different values for one or more parameters of at least one of the sequence of rules, classifying the defects based on results of said applying, and displaying results of said classifying such that a user can select values for the one or more parameters to be used with the inspection process.

18. The method of claim 10, further comprising selecting values for one or more parameters of a filter for the inspection process, wherein the filter is configured to remove nuisance defects from the inspection data.

19. The method of claim 10, further comprising tuning a threshold for the inspection process based on results of said identifying.

20. A system configured to generate an inspection process, comprising:
    an inspection system configured to generate data for a specimen at different values of one or more parameters, wherein the one or more parameters comprise one or more image acquisition parameters, one or more sensitivity parameters, or some combination thereof; and
    a computer system configured to:
    determine which of the different values produces the best data for the specimen;
    select the different values determined to produce the best data as values of the one or more parameters to be used for the inspection process;
    perform the inspection process two or more times on at least a portion of the specimen to produce two or more sets of additional inspection data; and
    identify defects that appear in a number of the two or more sets that is less than a predetermined number as nuisance defects.

* * * * *